US012678333B2

(12) United States Patent
Kim

(10) Patent No.: US 12,678,333 B2
(45) Date of Patent: Jul. 14, 2026

(54) EARWAX REMOVAL APPARATUS

(71) Applicant: OROGYLAB HEALTHCARE INC.,
Seoul (KR)

(72) Inventor: Young-Tae Kim, Seoul (KR)

(73) Assignee: OROGYLAB HEALTHCARE INC.,
Seoul (KR)

( * ) Notice: Subject to any disclaimer, the term of this
patent is extended or adjusted under 35
U.S.C. 154(b) by 536 days.

(21) Appl. No.: 18/215,243

(22) Filed: Jun. 28, 2023

(65) Prior Publication Data

US 2024/0000613 A1 Jan. 4, 2024

(30) Foreign Application Priority Data

Jun. 29, 2022 (KR) ........................ 10-2022-0079717

(51) Int. Cl.
*A61F 11/00* (2022.01)
*A61K 33/40* (2006.01)
*A61M 31/00* (2006.01)

(52) U.S. Cl.
CPC ............ *A61F 11/006* (2013.01); *A61K 33/40*
(2013.01); *A61M 31/00* (2013.01)

(58) Field of Classification Search
CPC ....... A61F 11/006; A61M 31/00; A61K 33/40
See application file for complete search history.

(56) References Cited

U.S. PATENT DOCUMENTS 5,425,355 A * 6/1995 Kulick ................... A61B 18/24
606/17
2020/0214894 A1* 7/2020 Kim ..................... A61M 3/0258

FOREIGN PATENT DOCUMENTS

KR 10-2017-0138318 A 12/2017

* cited by examiner

*Primary Examiner* — Mohamed G Gabr
(74) *Attorney, Agent, or Firm* — Nicholas Park

(57) ABSTRACT

Disclosed is an earwax removal apparatus comprising a head
portion moving from the inside to the outside of a wax
pocket and moving from the outside to the inside of the wax
pocket; and a remover removably mounted inside the wax
pocket and dislodging earwax from the tip of a scrubbing
head of the head portion and allowing it to fall into the
interior of the wax pocket. The earwax removal apparatus
may further comprise a dry-only head mountable on the
earwax removal apparatus and capable of entering an ear
canal and blowing air directly onto the walls of the ear canal.
The earwax removal apparatus may further comprise an oily
earwax removal portion configured to remove oily earwax
by injecting hydrogen peroxide into the ear canal through a
spray hole of the scrubbing head of the head portion.

15 Claims, 17 Drawing Sheets

Figure 28

EARWAX REMOVAL APPARATUS

CROSS-REFERENCE TO RELATED APPLICATIONS

This application claims priority under 35 U.S.C. § 119 to Korean Patent Application No. 10-2022-0079717 filed on Jun. 29, 2022, in the Korean Intellectual Property Office, the disclosures of which are incorporated by reference herein in their entireties.

BACKGROUND

Example embodiments of the present disclosure described herein relate to an earwax removal apparatus, and more particularly, relate to a method for operating an earwax removal apparatus that may safely and effectively remove dry ear wax from Easterners, wet ear wax from Westerners, and animal ear wax.

Earwax plays an important role in minimizing infections by physiologically inhibiting the entry of foreign bacteria and germs that may enter through the ear.

Even without artificial removing it, earwax is naturally removed by the motion of the jaw joint and surrounding muscles when a person speaks or chews food, which causes the skin in the ear canal to move, separating earwax from the skin and gradually pushing it out of the ear canal.

Therefore, it is not medically recommended to remove earwax artificially. This is due to the fact that swabs that are commonly used to remove earwax may push the earwax deeper into the ear canal, increasing the risk of adverse reactions.

However, despite these medical understandings and recommendations, earwax removal is more of a personal choice related to personal hygiene, especially, contrary to the medical explanation, it may stay in the ear for a very long time if not removed artificially, causing stuffiness, a foreign body sensation, discomfort and skin irritation when it moves, and the desire to remove it becomes very strong once the amount of earwax in the ear has accumulated to a certain point.

For this reason, people in most cultures around the world have been removing earwax for a long time, and most people around the world still remove it periodically as part of their daily routine.

Despite this general desire to remove earwax, traditional ear spoons, cotton swabs, and similar tools for removing earwax that are available on the market worldwide are limited in their ability to effectively and safely remove earwax on their own, as they rely on the user's senses to remove earwax since the user cannot see inside the ear. In addition, older adults and young children, who may have less fine motor control, may apply excessive force to the surface of the skin in the ear, causing cuts or inflammation, and may damage or perforate the eardrum if the tool is inserted deeper than necessary.

To solve the problem of not being able to see inside the ear, earwax removal tools with small USB cameras have recently been developed, but the disadvantage is that the ability to see may increase the motivation to remove the earwax completely, which may lead to removing more earwax than necessary. Furthermore, it is still a manual operation, so the safety of the operation is not secured, and the safety issue for the elderly and children is still unresolved.

On the other hand, in the case of a vacuum suction type earwax remover designed in the form of automatic removal through a vacuum suction method to solve the inconvenience of manual removal of earwax, it is necessary to sufficiently increase the suction vacuum pressure or sufficiently reduce the area of the suction port because the vacuum suction power must be sufficiently created. However, Increasing the vacuum pressure increases the potential risk of damaging the eardrum, so only limited suction pressure levels may be used, which means that earwax removal efficiency is relatively low. Therefore, it may quite effectively remove dry earwax, however, in the case of wet earwax, the removal efficiency decreases rapidly or is almost impossible to remove.

The traditional type of earpick has a spoon-like shape with a diameter of several millimeters at the end, which is easy to remove dry and wet earwax, and the handle part connected to the end is also designed to be very thin and long, within a few millimeters, so it is very easy to insert into the ear. The materials used are generally hard materials such as metal, wood, and plastic, which allow the tip of the tool to contact the skin surface of the ear canal and exert sufficient force on the skin surface. However, these tip structures and materials may exert significant pressure on the skin surface. The part of the end structure in contact with the skin surface is mainly the edge part of the spoon structure, and the force applied to the contact part is in the range of hundreds of grams to several kilograms, so that a high pressure of several tens of MPa may be applied to the skin surface at an instant. Therefore, if the force applied to the skin surface is not precisely controlled, it may cause great pain and inflammation due to damage to the skin surface. In particular, for people with poor skin conditions that make them very sensitive to external stimuli, or for the elderly or children who are more sensitive to irritation, it may be very irritating, so it is necessary to develop a very comfortable earwax removal tool that may automatically remove earwax with little irritation to the skin.

In the West, 92.4% of Caucasians, 96.9% of Afrimay Americans, and 98% of Europeans have wet earwax unlike their Asian counterparts, and about 50% of people over the age of 65 suffer from cerumen impaction (excessive earwax), a condition in which the ear is completely blocked by wax, which occurs periodically every few months.

The symptom of cerumen impaction is basically a very stuffy feeling in the ear, and otolaryngologic reports indicate a hearing loss of about 20 dB, which may cause major communication problems. It is also known to be a major disruption to the daily lives of the elderly, causing them to visit the doctor regularly to have their ear wax removed. Therefore, in order to prevent cerumen impaction for elderly people with symptoms of cerumen impaction, the number of times the user removes earwax within a certain period of time is monitored, and personal hygiene for earwax removal is recommended.

On the other hand, in the case of pets such as dogs and cats, periodic wax removal is recommended. A mechanical tool in the form of a cotton swab and a liquid type of wax dissolving agent are largely used to remove earwax from pets. As in the case of humans, a liquid form of earwax dissolving agent is recommended, but this method is also inconvenient to use, so mechanical tools in the form of cotton swabs are often used. However, when a tool in the form of a cotton swab is used, there is a side effect that earwax may be pushed into the ear when the tool is inserted, as same in humans, and it is not easy for the user to insert the earwax to a safe depth depending on the feeling and sense. Therefore, it is necessary to develop an earwax removal tool that may be used by setting a safe depth according to the size of the pet, which is safe and convenient, and which allows the pet to feel comfortable.

SUMMARY

Example embodiments of the present disclosure provide an earwax removal device that may safely and efficiently remove various forms of earwax.

According to an embodiment, an earwax removal apparatus comprises, a head portion moving from the inside to the outside of a wax pocket and moving from the outside to the inside of the wax pocket; and a remover removably mounted inside the wax pocket and dislodging earwax from the tip of a scrubbing head of the head portion and allowing it to fall into the interior of the wax pocket.

According to an embodiment, an earwax removal apparatus comprises, a head portion moving from the inside to the outside of a wax pocket and moving from the outside to the inside of the wax pocket; a remover removably mounted to the interior of the wax pocket and capable of dislodging earwax from a tip of a scrubbing head of the head portion and allowing it to fall into the interior of the wax pocket; and a head driving portion automatically driving the head portion.

According to an embodiment, an earwax removal apparatus comprises, a head portion movable from inside to outside and from outside to inside of a wax pocket, a remover removably mounted to the interior of the wax pocket and capable of dislodging earwax from a tip of a scrubbing head of the head portion and allowing it to fall into the interior of the wax pocket; and a user recognition portion disposed within reach of a user's fingers when the user grasps the earwax removal apparatus and allowing usage information of the earwax removal apparatus to be stored in the earwax removal apparatus or a server therein.

BRIEF DESCRIPTION OF THE FIGURES

The above and other objects and features of the present disclosure will become apparent by describing in detail embodiments thereof with reference to the accompanying drawings.

FIG. 28 is a system configuration diagram to illustrate the interaction between an earwax removal device according to the present invention and a server and a user terminal.

DETAILED DESCRIPTION

Figure 1:
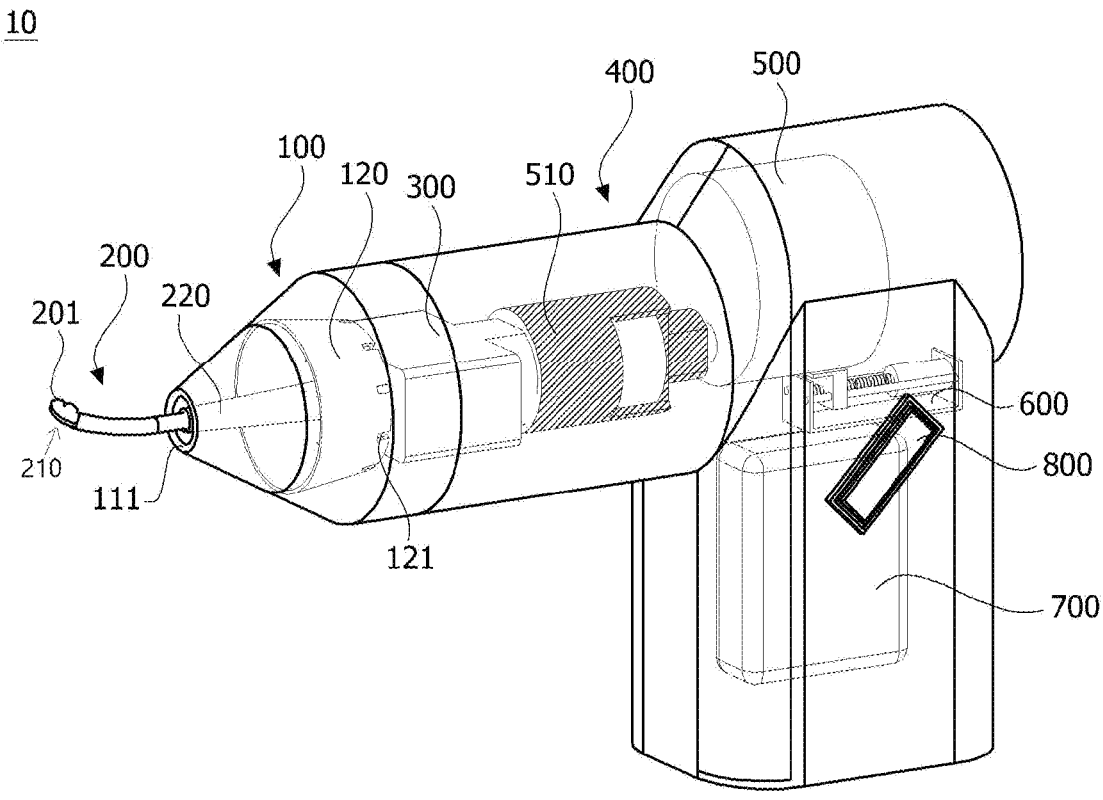
FIG. 1 is an internal perspective view of an earwax removal device according to the first embodiment of the present invention.

Below, example embodiments of the present disclosure will be described in detail and clearly to such an extent that an ordinary one in the art easily implements the inventive concepts.

The terminology used in this application is merely used to describe specific embodiments and is not intended to limit the invention. Expressions in the singular include the plural unless the context clearly indicates otherwise. In this application, the terms "includes" or "has" and the like are intended to designate the presence of the features, numbers, steps, actions, components, parts, or combinations thereof described in the specification, and not to preclude the possibility of the presence or addition of one or more other features, numbers, steps, actions, components, parts, or combinations thereof.

Unless otherwise defined, all terms used herein, including technical or scientific terms, shall have the same meaning as commonly understood by one of ordinary skill in the technical field to which the present invention belongs. Such terms, as defined in commonly used dictionaries, shall be construed to have a meaning consistent with their contextual meaning in the relevant art and shall not be construed to have an idealized or unduly formal meaning unless expressly defined in this application.

Preferred embodiments of the present invention will now be described in more detail with reference to the accompanying drawings. In describing the invention, the same reference numerals are used for identical components in the drawings and duplicate descriptions of identical components are omitted for ease of overall understanding.

Figure 2:
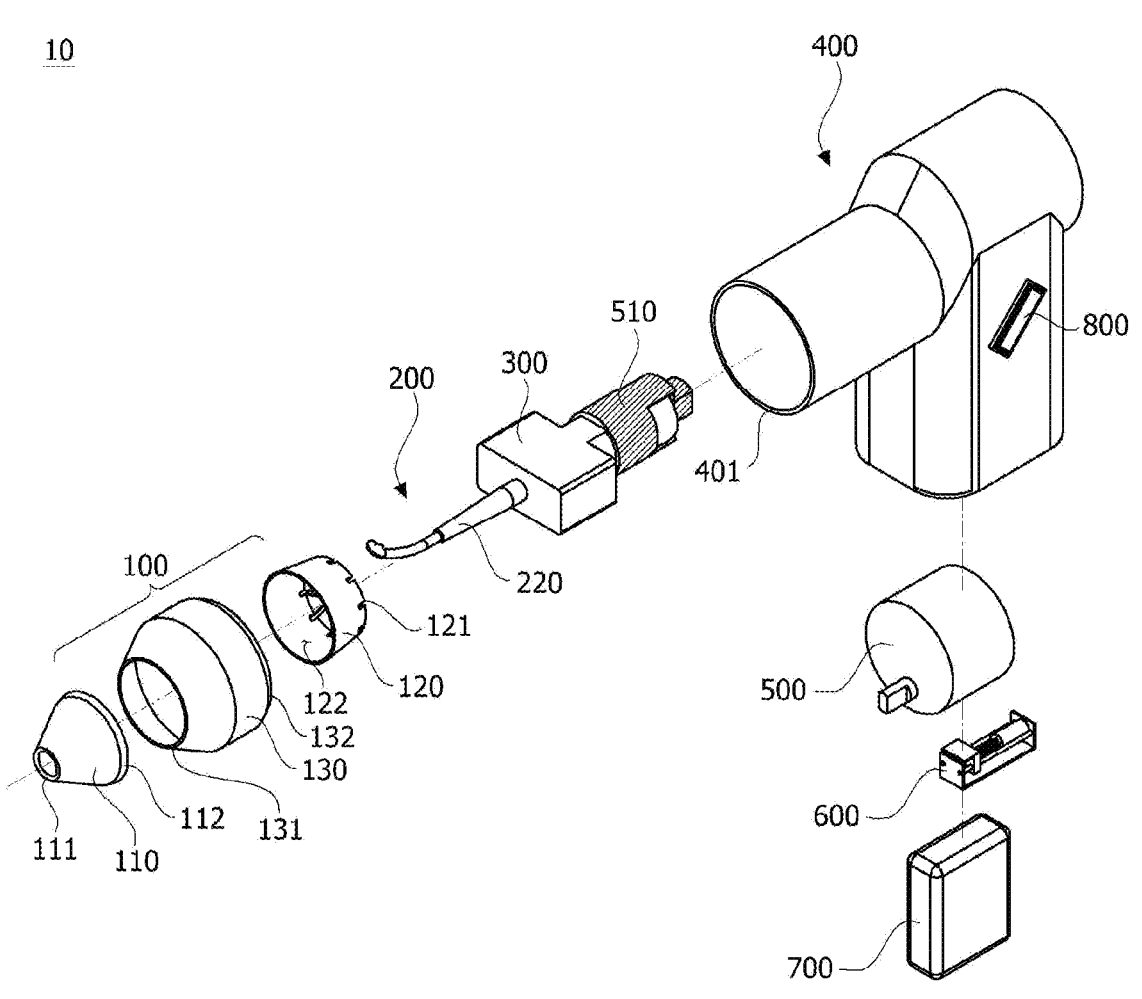
FIG. 2 is an exploded perspective view of an earwax removal device according to the first embodiment of the present invention.

FIG. 1 is an internal perspective view of an earwax removal apparatus according to the first embodiment of the present invention, and FIG. 2 is an exploded perspective view of an earwax removal apparatus according to the first embodiment of the present invention.

The earwax removal apparatus 10 according to the first embodiment of the present invention may include a wax pocket 120, a head portion 200, and a pump 300.

The pocket portion 100 may include a collection hole 111 and a outlet hole 121.

Further, the pocket portion 100 may include a contact member 110 having a collection hole 111 and an outlet hole 121 that is contact-supported in a user's ear canal.

In addition, the pocket portion 100 may further include the first connection member 130 connecting the contact member 110 and the main body 400.

More specifically, the contact member 110 may have a collection hole 111 and a mounting hole 112 formed on an opposite side of the collection hole 111.

The contact member 110 may be hollow on the inside and be sloped to increase in cross-sectional area from the collection hole 111 toward the mounting hole 112.

The contact member 110 may be cone-shaped, but is not limited thereto.

In particular, the collection hole 111 may be inserted into the entrance of the ear canal and be in intimate contact with the inner wall of the ear canal side. In one example, the contact may be such that an earphone is inserted into the entrance of the ear canal.

Here, the contact member 110 may be made of a rubber material. The rubber material may include, for example, but is not limited to, ordinary rubber, synthetic rubber, soft rubber, and the like.

Thus, by forming the contact member 110 having the collection hole 111 in direct contact with the user's ear canal from a rubber material, it has the effect of being more closely fitted to the user's ear canal.

As described above, the earwax removed from the wall of the ear canal by the collection hole 111, which is in close contact with the entrance of the ear canal, is not discharged to the outside, but may be more easily introduced into the apparatus.

Furthermore, the wax pocket 120 may include an outlet hole 121 and a one-sided opening 122 provided for exhausting air. More specifically, the the wax pocket 120 may have an aperture 122 at one end, and a outlet hole 121 may be formed on the opposite side of the aperture 122. A plurality of outlet holes 121 may be formed, and the plurality of outlet holes 121 may be further provided with a mesh member (not shown) in the form of a mesh. By providing a mesh member in each of the outlet holes 121 as described above, it is possible to prevent the outflow of earwax to the outside. The outlet holes 121 may be in the form of slots, for example, but are not limited to, and any structure that allows air to pass through is applicable.

The aperture 122 is coupled to the mounting hole 112 of the contact member 110 so that wax removed from the inner wall of the user's ear canal may pass through the collection hole 111 and be received within the wax pocket 120.

At the same time, air entrained with the earwax may be discharged to the outside through the outlet hole 121.

Thus, the mounting hole 112 may be formed to correspond to the opening 122 of the wax pocket 120.

Additionally, an insertion hole (not shown) may be formed in the center region of the wax pocket 120.

The insertion hole (not shown) in the center of the wax pocket 120 may be insertively mounted in the second connection member 220, which will be described later, so that the wax pocket 120 may be secured by the second connection member 220.

Further, a plurality of outlet holes 121 may be provided at predetermined intervals circumferentially around the perimeter of the center insertion hole (not shown) of the wax pocket 120, but are not limited thereto.

In addition, the first connection member 130 may be arranged to place the wax pocket 120 internally and may have the first connection hole 131 in connection with the mounting hole 112 side and a second connection hole 132 in connection with the aperture 401.

The head portion 200 is exposed to the outside through the collection hole 111 and may be arranged to have one or more air-blowing holes 201. A more detailed description of the head portion 200 will be provided later.

The pump 300 may supply air to cause air to flow outwardly through the air-blowing holes 201. Here, the pump 300 may be an air pump or an air fan.

The pump 300 may be disposed within the main body 400, and a portion of the pump may be disposed within the first connection member 130. Furthermore, the head portion 200 may be formed of a soft or hard material.

Further, the earwax removal apparatus 10 according to the first embodiment of the present invention may include a main body 400 that is connectively mounted to the first connection member 130.

The main body 400 may be arranged to have an aperture 401 provided on one side and a predetermined space connected to the aperture 401.

Meanwhile, the earwax removal apparatus 10 according to the first embodiment of the present invention may include a motor 500 arranged for rotating the head portion 200.

Here, the motor 500 may be, for example, a stepping motor.

More specifically, the motor 500 is coupled to one side of the head portion 200. Accordingly, the head portion 200 may be rotated by a rotational force transmitted from the motor 500.

That is, when the motor 500 is operated, the head portion 200 may rotate along the perimeter of the ear canal wall and contact the ear canal wall. Here, the head portion 200 may rotate 360 degrees along the perimeter of the ear canal wall, and the scrubbing head 210 may remove earwax adhering to the entire inner wall of the ear canal.

In particular, the motor 500 may cause the head portion 200 to rotate forward or reverse at preset reference angular intervals.

The motor 500 may be disposed within the main body 400 and may be disposed adjacent to the pump 300.

In particular, the motor 500 may include a connector 510 arranged to connect the pump 300 and the motor 500.

In one example, the first side of the connector 510 may include the first engagement portion that is matingly mounted to at least a portion of the pump 300 and the second engagement portion that is matingly mounted to at least a portion of the motor 500.

Further, the earwax removal apparatus 10 according to the first embodiment of the present invention may include a drive portion 600 arranged to move the head portion 200 forward and backward.

The drive portion 600 may include a linear guide. The linear guide may be a motorized transportation apparatus, such that driving the drive portion 600 may cause it to move forward and backward at a preset speed. Here, the forward or backward movement may be repeated.

The drive portion 600 may be coupled to the head portion 200, and may be arranged to slidingly move the head portion 200 into the ear canal of a user, and may be moved at a preset speed.

More specifically, the drive portion 600 may be coupled to one side of the motor 500.

That is, the motor 500 may be moved at a preset speed by driving the drive portion 600.

As described above, the head portion 200 is connected to the pump 300, the pump 300 is connected to the motor 500 by the connector 510, and the motor 500 is connected to the drive portion 600 such that the motor 500, the pump 300, and the head portion 200 may be slidingly moved forward or backward by driving the drive portion 600.

Furthermore, the motor 500, the pump 300, and the head portion 200 are integrated by the connector 510 so that the motor 500, the pump 300, and the head portion 200 may be simultaneously moved forward or backward at a preset speed by the drive portion 600, i.e., the linear guide.

In particular, the rotational force transmitted from the motor 500 rotates the pump 300 by the connector 510, thereby enabling the head portion 200 connected to the pump 300 to rotate.

Thus, the head portion 200 may be moved inside the ear canal of the user by the drive portion 600, wherein the depth at which the head portion 200 is moved inside the ear canal may be approximately 15 to 20 millimeters.

As described above, the head portion 200 enters the user's ear canal at a constant speed according to a set speed, and the scrubbing action may begin at the entrance of the ear opening and reciprocate between certain depths inside the ear canal to continuously remove earwax.

In particular, by limiting the entry depth of the head portion 200 to approximately 15 to 20 mm, it is possible to remove only the earwax that has been pushed to the outer part of the ear canal, so that the physiological net function of the earwax formed inside the ear canal may be maintained as much as possible.

For users who are sensitive to skin irritation, such as elderly and disabled people who have difficulty controlling small forces and movements, they may feel great pain if the head portion 200 moves quickly while in contact with the skin. Therefore, by automatically adjusting the forward and backward speed of the head portion 200 inside the ear canal at a slow and constant speed by the drive portion 600, the user does not feel much inconvenience and the user's earwax may be automatically removed.

On the other hand, a battery 700 may be disposed inside the main body 400 to electrically connect with the pump 300, the motor 500, and the drive portion 600 to supply power.

Furthermore, the earwax removal apparatus 10 according to the first embodiment of the present invention may include a user recognition portion 800 arranged to store and recognize information of a user's use of the apparatus.

The user recognition portion 800 may be a fingerprint recognition apparatus (fingerprint sensor), and may be disposed on an outer surface of the main body 400.

The user recognition portion 800 may be arranged to store various information of the user, such as the number of times the user uses the apparatus, the time of use, etc., inside the apparatus by placing it in a position where the user's thumb may reach when the user grasps the apparatus 10, such as a pre-registered user or automatic registration of the user when using the apparatus.

Figure 4:
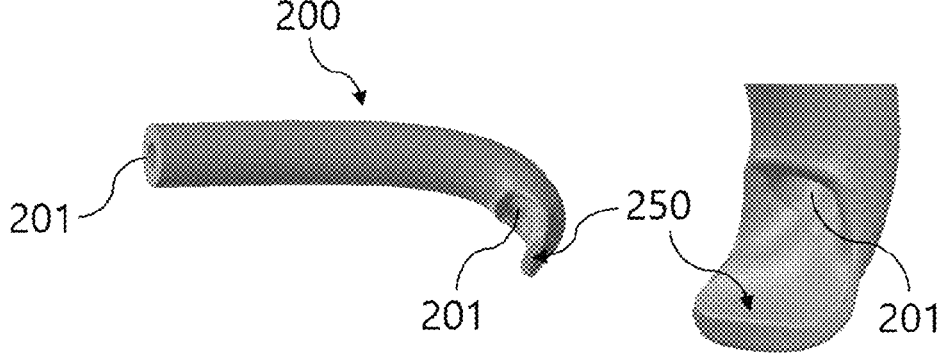
FIG. 4 is a variation of the head section of FIG. 3.

The user recognition portion 800 may be replaced with any kind of manipulator or apparatus, including a miniature jog switch or the like, so that the speed of movement of the scrubbing head 210 and the spoon-shaped tip 250 (as shown in FIG. 4) and the like may be controlled directly by the user, using a thumb, based on the user's subjective sensation of pain when the scrubbing head 210 and the spoon-shaped tip 250 (as shown in FIG. 4) and the like contact the skin of the ear canal. The speed of movement of the scrubbing head 210 and the tip 250 in the form of a spoon may be directly controlled by the user, so that it may be controlled at a speed that the user feels comfortable with, and the speed information finally selected by the user may be stored inside the earwax removal apparatus 10 or on a server or the like connected in real time through an application associated with the earwax removal apparatus 10, so that it may be automatically applied when the user reuses the earwax removal apparatus 10.

In addition, the stored user information may be arranged to be stored on an online network through a wireless transmission apparatus such as Wi-Fi.

In particular, the user may check his/her usage information stored on the online network using an application on the smartphone, and the application may be arranged to analyze the user's information and provide appropriate warnings or suggestions by means of voice and text.

In addition, a separate storage apparatus and information analysis software may be used inside the apparatus to deliver warnings or recommendations to the user by voice through the built-in speaker.

As described above, the warning and recommendation method for the user based on the user's apparatus usage information may be linked to a management program for the purpose of preventing cerumen impaction for users with frequent cerumen impaction, and in the case of users with frequent cerumen impaction, a notification section having a notification function to encourage periodic use of the apparatus may be added to the apparatus.

In other words, the user recognition portion 800 may be arranged to give appropriate alarms and recommendations to the user by means of voice information and text messages through a smartphone application and a plurality of apparatus provided within the automatic earwax removal apparatus 10.

In addition, a switch (not shown) for operating the apparatus 10 may be provided on an outer surface of the main body 400, and the apparatus 10 may be operated according to an on/off operation of the switch.

In addition, a mode selector (not shown) for selecting an automatic mode or a manual mode of the earwax removal apparatus 10 may be provided on the outer surface of the main body 400 as needed.

Figure 3:
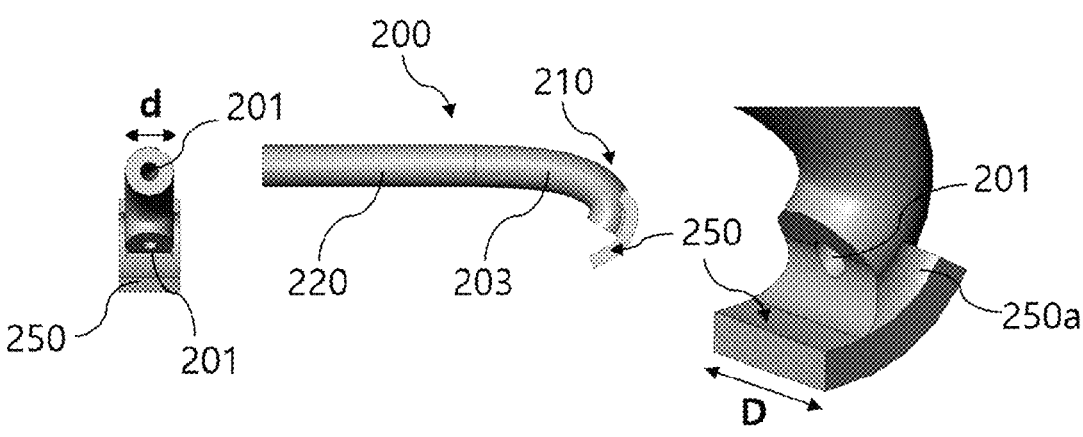
FIG. 3 is a drawing to illustrate the head section of the first embodiment of the present invention.

FIG. 3 is a drawing to illustrate the head portion 200 of the first embodiment of the present invention.

The head portion 200 in FIG. 3 may include a scrubbing head 210 having an air-blowing hole 201 and curvedly formed to contact on the wall surface of the ear canal.

The scrubbing head 210 may be rounded at one end of the head portion 200, and may contact and scrub the ear canal wall to dislodge the user's earwax from the ear canal wall.

Additionally, the head portion 200 may include a flow passage member 203 having an air passage connected to the air-blowing hole 201.

The flow passage member 203 may be formed to have a predetermined length to allow the scrubbing head 210 to be inserted into the ear canal to a predetermined depth to remove earwax.

One side of the flow passage member 203 is fluidly and movably connected with the pump 300. Accordingly, air supplied from the pump 300 may flow through the air passages of the flow passage member 203 and out into the ear canal through the air-blowing hole 201.

Here, the head portion 200 may further include the second connection member 220 connecting the pump 300 and the flow path member 203.

The second connection member 220 may have a predetermined length and may have a flow passage formed therein so that air supplied by the pump 300 flows into the flow passage member 203.

In particular, in the first embodiment of the present invention, the bent end of the scrubbing head 210 (i.e., the part where the air-blowing hole 201 is formed from which air is discharged) has a protruding spoon-shaped tip 250 (as shown in FIG. 4) that is suitable for scraping the wall of the ear canal and digging out wet earwax.

The head portion 200 according to the first embodiment of the present invention is capable of efficiently removing both dry and wet earwax, and in particular, the tip 250 of the scrubbing head 210 is preferably formed with a curved surface facing away from the ear to allow for more efficient digging or scooping of wax-like wet earwax. Additionally, the tip 250 may be formed in a shape that includes a plurality of edges.

It is desirable to minimize the cross-sectional area of the tip 250 to ensure that the tip 250 of the scrubbing head 210 does not push earwax when the head portion 200 enters the ear canal. To this end, it is preferred that the width D of the curved surface of the tip 250 is no larger than necessary relative to the cross-sectional width d of the tip 250. For example, the width D of the curved surface of the tip 250 is preferably about 130% or so (D/d=130% or so) relative to the cross-sectional width d of the area in which the air-blowing hole 201 is formed.

In FIG. 3, non-descriptive markings 250*a* are wings protruding from the end of the scrubbing head 210 in a direction opposite to the direction of formation of the tip 250.

As the scrubbing head 210 enters the ear canal, rotates to the left (or right) at a predetermined angle, and then exits the ear canal, the tip 250 digs or scoops out the earwax, and the wings 250*a* may additionally dig or scoop out the surrounding earwax.

FIG. 4 is a variation of the head portion 200 of FIG. 3.

Compared to the head portion 200 of FIG. 3, the head portion 200 of FIG. 4 not only lacks wings 250*a*, but also differs somewhat in the shape of the tip 250. The difference in shape is that the tip 250 of the head portion 200 of FIG. 3 is angled to have a vertex, whereas the tip 250 of the head portion 200 of FIG. 4 is rounded.

While the head portion 200 of FIG. 4 is shown without wings 250*a*, the tip 250 of the head 200 of FIG. 4 may also be shown with wings 250*a* as in FIG. 3.

As described above, the head portion 200 of FIGS. 3 and 4 may be arranged to be exposed to the outside via a collection hole 111, which may be disposed within the wax pocket 120 to penetrate the contact member 110 and the first connection member 130. In particular, the cross-sectional area of the collection hole 111 may be formed larger than the cross-sectional area of the head portion 200, and the head portion 200 may be arranged to have a predetermined spacing from the edge of the collection hole 111, so that earwax may pass through the collection hole 111 and enter the wax pocket 120 through the predetermined area formed by the predetermined spacing.

In particular, the scrubbing head 210 and the flow passage member 203 may be formed of soft or hard materials. In this case, the soft and hard materials may have an approximate hardness of Shore A 30 to 90. More specifically, the head portion 200 may be formed of a soft or hard material having an approximate hardness of Shore A 30 to 90, such that the contact force with the inner wall of the ear canal, i.e., the skin surface, is controlled to a predetermined range.

In particular, the flow passage member 203, which is formed to bend toward the ear canal wall, is formed of a soft or hard material with elastic resilience, so that when the scrubbing head 210 connected to the flow passage member

203 contacts the ear canal wall, the flow passage member 203 is stretched from its original bent shape according to the diameter of the user's ear canal, and elastic energy may be accumulated by the bending stiffness of the flow passage member 203.

This elastic energy may be applied to the ear canal wall in the form of an elastic contact force via the scrubbing head 210 in contact with the ear canal wall.

In other words, the flow passage member 203 is made of a soft or hard material having a predetermined stiffness and is formed to bend at a predetermined angle toward the ear canal wall, so that the scrubbing head 210 may easily contact the ear canal wall, and the elastic contact force applied to the ear canal wall may be effectively limited to a predetermined value or less even when the flow passage member 203 is fully stretched by the user's force.

Therefore, when the flow passage member 203 is fully stretched by the user's force, the elastic contact force applied to the ear canal wall becomes a maximum value, and since the maximum value of the elastic contact force is limited to a predetermined value or less, it is possible to minimize physical stimulation by scrubbing the ear canal wall.

Here, the soft and hard materials may be, for example, but not limited to, Silicone Rubber, Thermoplastic Rubber (TPR), Polyvinyl Chloride (PVC), and Polyurethane (PU).

The head portion 200 may be rotated forward or backward by the motor 500 at a preset reference angle interval, where each preset reference angle is a step rotation, and the head portion 200 may be rotated by repeating a plurality of forward and backward rotations within one step rotation (in place).

That is, the head portion 200 may complete a 360-degree rotation by repeating each step rotation in either the forward or reverse direction, and may repeat a plurality of forward and reverse rotations within a single step rotation (in place).

For example, if the set angle is 5°, the head portion 200 may be rotated 360° in 72 steps, with each 5° rotation being 1 step, and within each step rotation (in place), the head portion 200 may be rotated multiple forward and backward rotations.

This means that the inner circumference of the ear canal may be divided into 72 zones and rotated 360° (degrees) in 5° (degrees) increments of forward or reverse rotation and that one cycle of forward and reverse rotation may be repeated about 5 times in one step, and another 5 times in the next step, all within 72 zones, 360° (degrees). Here, that 1 cycle is not limited to 5 cycles.

As described above, the scrubbing head 210 rotates 360 degrees forward and backward along the circumference of the ear canal wall to scrub the ear canal wall, thereby weakening the adhesion of wet earwax firmly attached to the inner wall of the ear canal and the interlocking of dry earwax.

At this time, the earwax may be more easily removed by releasing air into the ear canal wall through the air-blowing hole 201.

In the present invention, when air pressure is applied through the air-blowing hole 201 to remove earwax adhering to the ear canal wall, the earwax may be removed with minimal physical irritation to the ear canal skin surface.

However, in the case of earwax that is firmly adhered to the skin surface of the ear canal, it may be difficult to completely remove the earwax using only air pressure. Therefore, by utilizing the scrubbing head 210 with the protruding tip 250 to densely scrub the entire surface of the inner wall of the ear canal while simultaneously applying air pressure through the air-blowing hole 201, the earwax may be removed more easily and quickly.

The dry earwax described above has the characteristic of being easily broken by mechanical pressure, so that it may easily fall off the surface of the ear canal by the scrubbing action alone, and may be easily discharged into the wax pocket 120 by the air blowing pressure.

The wet earwax described above has the effect of causing quick drying of the wet earwax by the air discharged through the air blowing hole 201 of the present invention, thereby generating surface tension along the boundary of the earwax attached to the skin, so that the earwax easily falls off the skin.

Therefore, the wet earwax is easily separated from the skin by the ejected air, and at the same time, through the drying process, it is changed to a property similar to dry earwax and may be easily crushed by the scrubbing action.

In other words, by simultaneously scrubbing and blowing air with the head portion 200, the removal efficiency of dry earwax and wet earwax may be increased.

Furthermore, as described above, the scrubbing action of the head portion 200 may separate the earwax from the skin surface of the ear canal and discharge it out of the ear canal by utilizing minimal physical force with the limited contact force, and capture it in the wax pocket 120.

Figure 5:
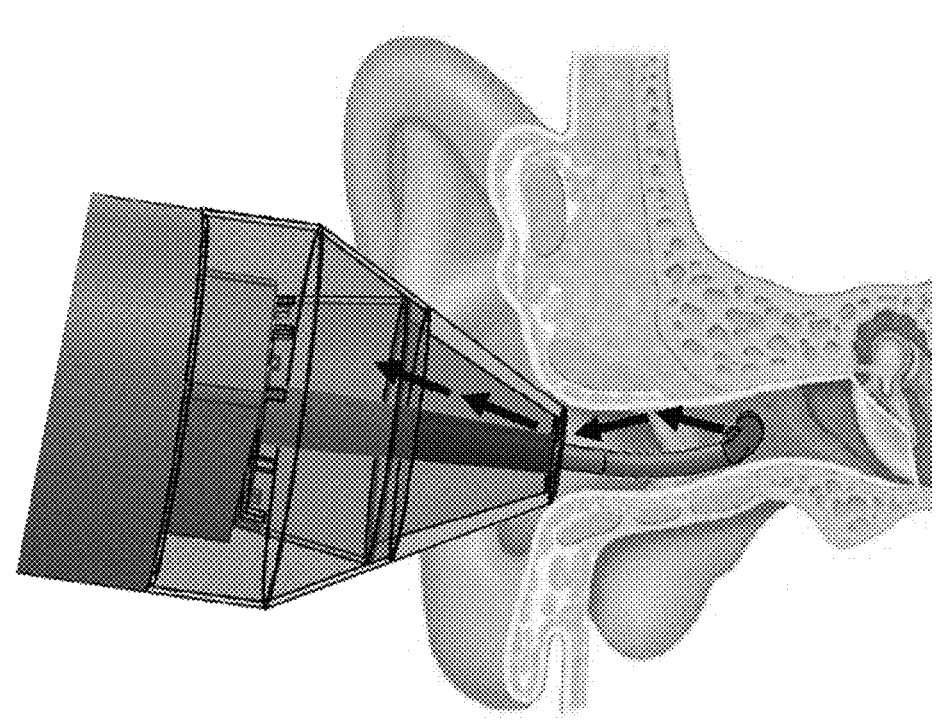
FIG. 5 is a state-of-use diagram to illustrate the use of an earwax removal device according to the first embodiment of the present invention.

FIG. 5 is a state-of-use diagram to illustrate the use of an earwax removal apparatus according to the first embodiment of the present invention.

Referring to FIG. 5, the head portion 200 of FIGS. 3 and 4 may be arranged to bend toward the ear canal wall such that at least a portion thereof contacts the ear canal wall. More specifically, the flow passage member 203 may be arranged to bend toward the ear canal wall such that the scrubbing head 210 of the head portion 200 contacts the ear canal wall.

When the collection hole 111 side is in contact with a portion of the user's ear, air exiting the air-blowing hole 201 may hit the tip 250, reflect, and flow through the user's ear canal, and travel through the collection hole 111 to the outlet hole 121 side.

More specifically, the air discharged from the air-blowing hole 201, along with the user's earwax, may pass through the collection hole 111 and enter the opening 122 of the wax pocket 120 connected to the mounting hole 112, the earwax may be stored in the wax pocket 120, and the air may be discharged to the outside through the outlet hole 121.

In particular, the air-blowing hole 201 may be formed to have an angle in the range of approximately 45 degrees to 90 degrees relative to an imaginary center axis line in the longitudinal direction of the head portion 200.

By forming the air-blowing hole 201 as described above, air flowing out of the air-blowing hole 201 may hit the tip 250, reflect, and flow toward the collection hole 111.

Thus, earwax adhering to the wall of the ear canal may be removed by the air pressure discharged through the air-blowing hole 201, out of the ear canal (toward the collection hole).

In this case, the air pressure generated may be approximately 7 to 14 kPa or 9 to 11 kPa or 10 kPa or less, but is not limited thereto.

By forming the spoon-shaped tip 250 (as shown in FIG. 4) at the end of the scrubbing head 210 as described above, it is possible to discharge air out of the ear canal (toward the collection hole), thereby avoiding the problem of direct pressure being applied to the eardrum. In addition, it is possible to prevent discomfort that the user may feel due to the air pressure that may be applied to the eardrum.

Furthermore, by discharging air as described above, it is possible to remove moisture that has entered the inside of the user's ear canal during washing and bathing from the outside of the ear canal and evaporate.

The automatic earwax removal apparatus 10 according to the first embodiment of the present invention used in this manner may further include a moisturizing apparatus (not shown) arranged to provide moisture by spraying a trace amount of moisture toward the wall of the ear canal.

When moisture is supplied by the hydration apparatus as described above, in the case of dry earwax, the supplied moisture may weaken the adhesion of the earwax, thereby reducing pain during earwax removal, and may improve the scrubbing effect of the scrubbing head 210.

Here, the moisture may include, but is not limited to, saline solution, water, and the like.

Figure 6:
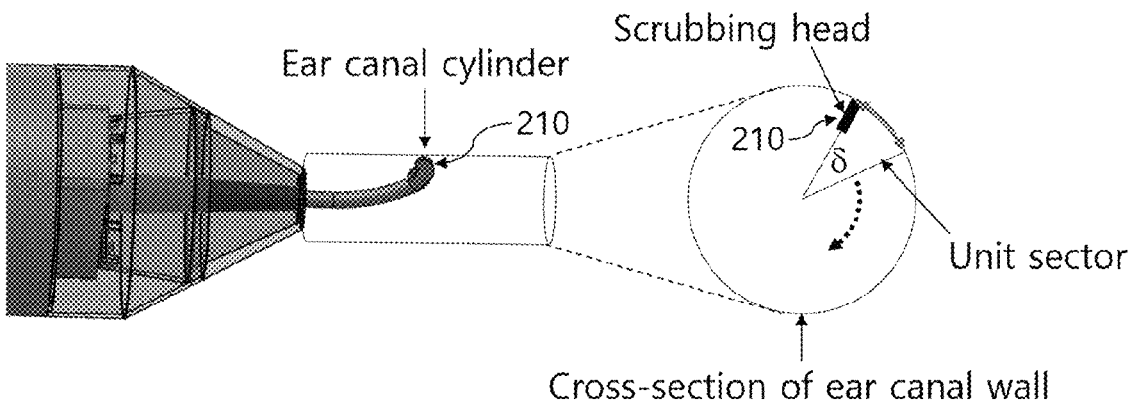
FIG. 6 is a diagram to illustrate the operation of removing dry earwax by an earwax removal device according to the first embodiment of the present invention.

FIG. 6 is a drawing to illustrate an operation of removing dry earwax by an earwax removal apparatus according to the first embodiment of the present invention.

Dry earwax may be adhered to the skin surface of the ear canal, or may be mobile inside the ear canal if it is detached from the skin.

Therefore, in the case of dry earwax adhering to the skin surface, it is necessary to physically scrub it off the ear canal surface, and in the case of dry earwax adhering to the skin surface, it is efficient to remove it by blowing it out of the ear using low air pressure.

To this end, the earwax removal apparatus according to the first embodiment of the present invention physically rubs the dry earwax by repeating a number of forward and reverse rotations of the scrubbing head 210 within a unit sector (unit arc) having a predetermined inner angle (δ) to cause the dry earwax to fall from the ear canal wall surface. At the same time, blowing is performed simultaneously to remove the earwax that has fallen off the surface of the ear canal by blowing it into the interior of the apparatus connected to the ear canal.

At this time, the scrubbing head 210 enters the outermost circumference of the ear canal (outside the ear) where the dry earwax is formed and removes it.

Since the circumference of the ear canal may be divided into predetermined unit sectors, for every unit sector, the scrubbing head 210 operates in the same sequential manner to remove the dry earwax in the ear canal.

Once a full circumference of earwax (e.g., dry earwax) has been removed, the scrubbing head 210 is advanced a unit depth into the ear canal to remove another circumference of dry earwax using the tip 250 in the same manner.

When the method described above is applied to the entire circumference of the ear canal, dry earwax may be removed from the surface of the entire ear canal (assuming a cylinder) at a depth of approximately 15 mm or less.

The dry earwax removal operation described above is further explained as follows.

The motion of the earwax removal apparatus according to the first embodiment of the present invention may be configured to be controlled by two parameters of size.

The first parameter is an angle (δ) of the unit sector, and the second parameter is a scrubbing speed at which the scrubbing head 210 scrubs the ear canal wall based on the angle of the unit sector.

Here, the angle δ of the unit sector may be approximately in the range of 5° to 20°.

If the angle of the unit sector is smaller than 5°, the time required to scrub the ear canal wall increases, making it difficult to remove earwax efficiently, and if the angle of the unit sector is larger than 20°, the friction force acting on the ear canal wall increases, causing unexpected skin irritation on the ear canal wall.

On the other hand, the scrubbing speed may be approximately 5 mm/s to 50 mm/s. If the scrubbing speed is less than 5 mm/s, the time required to scrub the ear canal wall increases, making it difficult to remove earwax efficiently, and if the scrubbing speed is greater than 50 mm/s, the friction force acting on the ear canal wall increases, causing unexpected skin irritation on the ear canal wall.

However, this is an example for convenience of explanation, and the physical conditions of the scrubbing head 210 to satisfy both of these should also be considered, which may be varied according to the needs of the user, and is not intended to limit the scope of the present invention.

Figure 7:
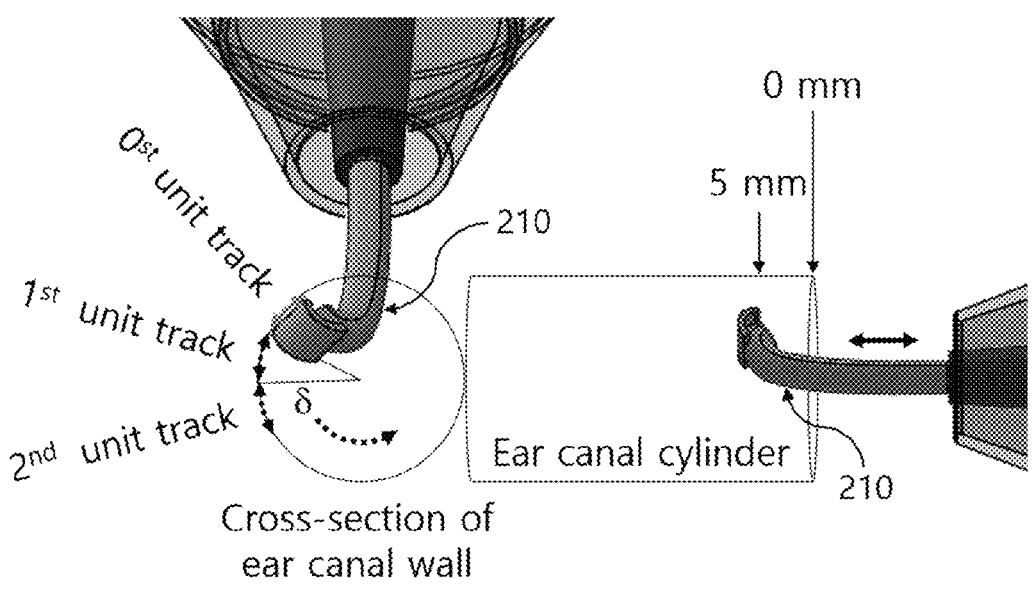
FIG. 7 is a diagram to illustrate the operation of removing wet earwax by an earwax removal device according to the first embodiment of the present invention.

FIG. 7 is a diagram to illustrate the operation of removing wet earwax by an earwax removal apparatus according to the first embodiment of the present invention.

Wet earwax is formed due to a relatively large amount of secretion from the cerumen glands on the wall of the ear canal, which accumulates before it dries and forms a wide, thick layer in the ear canal space.

Therefore, it is effective to remove the accumulated earwax by digging or scooping it out from the outside of the ear canal little by little rather than physically rubbing it.

Further, because wet earwax, unlike dry earwax, builds up in a way that blocks the entire ear canal opening, it is necessary to minimize the tip 250 of the scrubbing head 210 from pushing the earwax inward when the scrubbing head 210 is advanced into the ear canal.

Accordingly, when the scrubbing head 210 is first (initially) advanced into the ear canal, it may be advanced a unit depth (e.g., approximately 5 mm) into the ear canal, and then rotate to the right (or left) by an angle δ to move to the "1st track" and then move the scrubbing head 210 out of the ear canal via the 1st track to remove the earwax on the 1st track with the tip 250. In practice, it is not always possible to enter the scrubbing head 210 on the "zeroth track" each time the earwax removal apparatus is used, so it may be understood that the first track entered is the "zeroth track," i.e., the position of the "zeroth track" is variable rather than fixed.

Then, the second time the scrubbing head 210 enters the ear canal, it enters the same depth into the first track that has already been cleared once, and then rotates to enter the next track, the second track. After entering the second track, the scrubbing head 210 is moved out of the ear canal to remove the wax in the second track with the tip 250.

When entering the second track, the scrubbing head 210 enters via the first track where a large portion of the earwax has already been removed in the previous removal with only the same depth as the first track, thus it has the advantage of entering the second track without pushing the earwax inward.

By repeating this method, the wet wax in all tracks of one circumference (i.e., the circumference of the predetermined unit depth) may be removed.

Once all tracks in the outermost first circumference of the ear canal have been removed, the depth of entry may be increased by a unit depth to remove all tracks in the second circumference in the same manner as described above.

When the method described above is applied sequentially to the entire cylinder of the ear canal, the wet earwax may be removed very effectively with minimal inward pushing of the wet earwax.

The 5 mm mentioned in the above description of FIG. 7 is an example, but not a limitation.

In other words, the head portion 200 (in particular, the scrubbing head 210) may perform an earwax removal operation in which it enters a preset unit depth through any one of the plurality of tracks against a wall surface of an ear canal comprising a plurality of tracks, moves to an adjacent track by rotating a certain angle (δ), and then retreats to the outside of the ear canal through that adjacent track. More specifically, in the earwax removal operation, the head portion 200 (in particular, the scrubbing head 210) may, in the first entry, enter a predetermined unit depth through any one of the plurality of tracks, rotate to an adjacent track, and retreat to the outside of the ear canal through that adjacent track, and, in the second entry to the last entry, enter the same depth through the previously retreated track, rotate to an adjacent track, and retreat to the outside of the ear canal through that adjacent track.

On the other hand, the head portion 200 (in particular, the scrubbing head 210) may repeat the above-described earwax removal operation on all tracks at the current depth entered and on all tracks at subsequent depths following each subsequent entry by a unit depth.

Referring again to the above-described operation of removing wet earwax using the head portion 200 (in particular, the scrubbing head 210), the advancing step of entering the head portion 200 (in particular, the scrubbing head 210) into the ear canal at a preset first depth; a rotation step in which, after advancing to the first step depth, the scrubbing head 210 is rotated at a preset angle so that the leading edge of the scrubbing head 210 contacts the inner wall of the ear canal of the imaginary first track; and a retraction step in which, with the leading edge of the scrubbing head 210 in contact with the inner wall of the ear canal due to the rotation, the scrubbing head 210 is retracted to the interior of the wax pocket to scrape and remove the inner wall earwax of the imaginary first track; the first-depth earwax removal step of removing earwax on the corresponding virtual track at 360 degrees of the inner wall of the ear canal at the first depth by repeatedly entering, rotating, and reversing through the virtual track from which the earwax is removed; and, when the first-depth earwax removal is completed, entering to a preset second depth and repeating the steps of entering, rotating, and reversing to remove the earwax up to the second depth, and repeating the steps described above to remove the earwax up to the preset depth.

Figure 8:
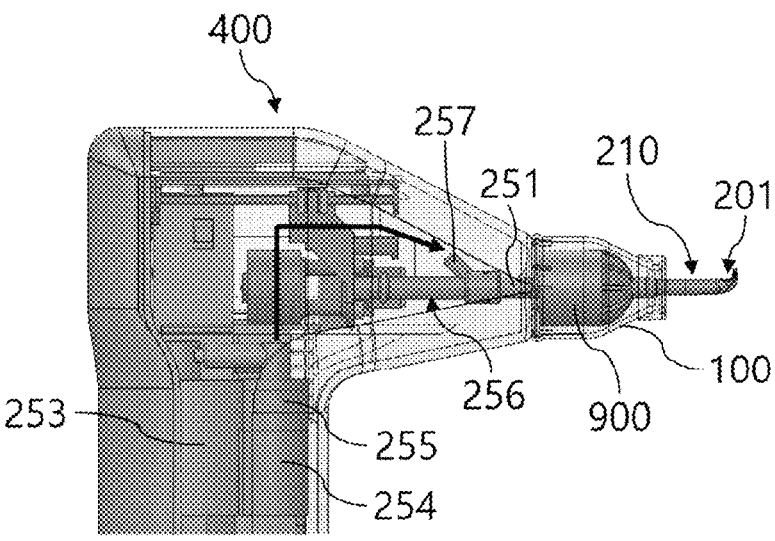
FIG. 8 is a drawing of an earwax removal device working as a dryer for the ear canal according to the first embodiment of the present invention.
Figure 9:
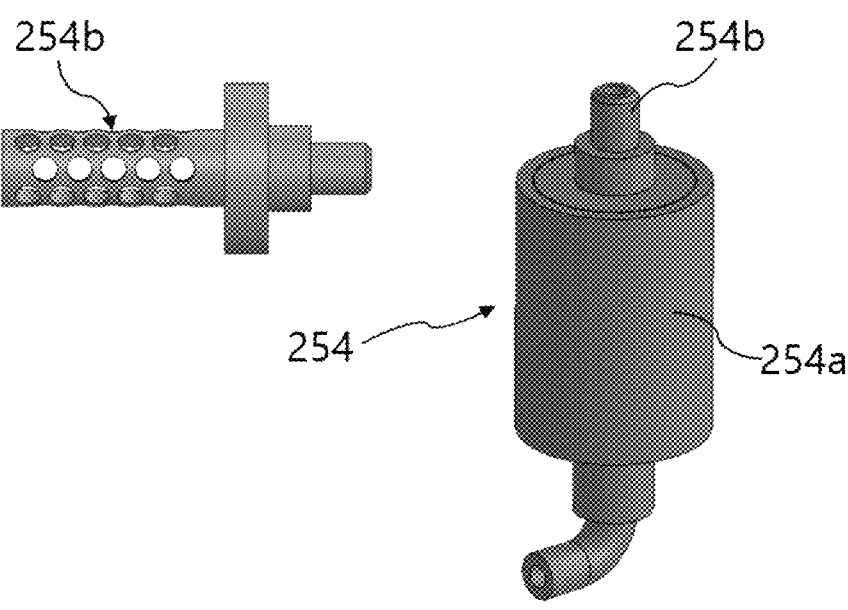
FIG. 9 is a drawing to illustrate the internal micro-silencer shown in FIG. 8.

FIG. 8 is a drawing of an earwax removal apparatus according to the first or second embodiment of the present invention converted into a dryer for the ear canal, and FIG. 9 is a drawing to illustrate the micro-silencer shown in FIG. 8.

The earwax removal apparatus according to the first or second embodiment of the present invention may be used to realize the dryer for the ear canal of FIG. 8, that is, after removing the earwax inside the ear canal with the earwax removal apparatus according to the first or second embodiment of the present invention, the scrubbing head 210 may be removed and used in combination with the dry-only head 20.

In South Korea, about 2 million people are infected with otitis externa (outer ear infection) every year, and the incidence is evenly distributed among all age groups, with about the same number of patients every month, but it increases slightly in summer (National Health Insurance Service).

In the United States, about 10 percent of the population is infected with otitis externa each year, and it is caused by water in the ear canal after swimming or showering and neglect of moisture. In addition, minor damage and inflammation of the ear canal skin occurs due to the use of metal earplugs. The use of cotton swabs with bacterial growth due to high humidity in the summer increases the rate of infection.

American and Korean otolaryngologists recommend using a hair dryer after swimming or showering to dry the inside of the ear, but drying the relatively small ear canal with a hairdryer is not effective, and a large hairdryer is not easy to carry.

Therefore, the dryer for ear canal in the present invention should be equipped with a micro-dryer function that may directly dry the ear canal using low-pressure air from the air pump 253. In addition, a micro heater 255 is embedded to adjust the temperature so that warm air may be blown in winter to make it comfortable to use.

Assuming that the scrubbing head 210 shown in FIG. 8 is replaced with a dry-only head 20, the air from the air pump 253 may be passed sequentially through the micro-silencer 254 and the micro-heater 255 to become warm air and applied to the dry-only head 20.

To minimize heat loss, the micro heater 255 is located in the outlet flow path of the micro silencer 254 so that warm air may be applied directly to the air blast opening 261 of the dry-only head 20.

By controlling the voltage or current applied to the microheater 255, the temperature of the air may be controlled, and by controlling the operating voltage and current of the air pump 253, the air pressure and intensity may be adjusted.

On the other hand, in the case of an ultra-compact air pump, the diaphragm type air pump 253 is used in terms of the efficiency of pressure formation, but in this case, pneumatic noise caused by compressed air is generated. The level of this noise is around 50 dB, which is about the noise level of a quiet office.

Therefore, the ear canal dryer of the present invention includes a micro silencer (muffler) 254, which reduces the compressed air noise by about 10% (in dB), so that the intensity of the noise may be reduced to a level of 45 dB, which is not very annoying.

That is, a micro-muffler 254 may be installed between the air pump 253 and the micro-heater 255.

The micro-silencer 254 comprises a porous pipe 254b inside a outer body 254a of the silencer 254, as illustrated in FIG. 9.

Inside the outer body 254a of the micro-silencer 254, a space exists between the porous pipe 254b and a wall surface of the main body, into which a sound-absorbing material (not shown) may be inserted.

Therefore, the micro-silencer 254 may be manufactured in the form of inserting a pipe-shaped sound-absorbing agent (not shown) made of various fabrics such as cotton, wadding, etc. into the porous pipe 254b and inserting it into the silencer outer body 254a.

When compressed air is applied to the inlet of the micro-silencer 254, the impact sound pressure of the compressed air passing through the silencer is absorbed and dissipated by the sound absorber through a plurality of air holes in the porous pipe 254b open to the sound absorber, so that attenuation of the noise occurs and the air flow is discharged through the outlet.

On the other hand, in the case of wet (oily) earwax of Westerners, it gradually hardens when left for a long time without removal, so it cannot be easily removed physically. Therefore, a hydrogen peroxide solution or the like that may safely dissolve the hardened wet earwax is used, and in the present invention, as shown in FIG. 8, such hydrogen peroxide is injected into the interior of the scrubbing head connector 256 through an opening or the like provided on the outside of the main body 400, so that the hydrogen peroxide solution may be sprayed into the interior of the ear canal using the dry function of the earwax removal apparatus. The scrubbing head connector 256, to which the head attachment rod 251 is connected, has a space of a certain size inside it, and the space is connected to the scrubbing head connector 256 air inlet 257 through an internal passage. Thus, when the dry function is operated, the dynamic pressure of the head attachment rod 251 and the scrubbing head 210 inner passage is reduced, so that the hydrogen peroxide solution in the space inside the scrubbing head connector 256 moves through the head attachment rod 251 and the scrubbing head 210 inner passage and is sprayed into the ear canal through the air-blowing hole 201. The shape and size of scrubbing head connector 256 may be varied and may be mounted outside of the main body 400 if desired.

Figure 10:
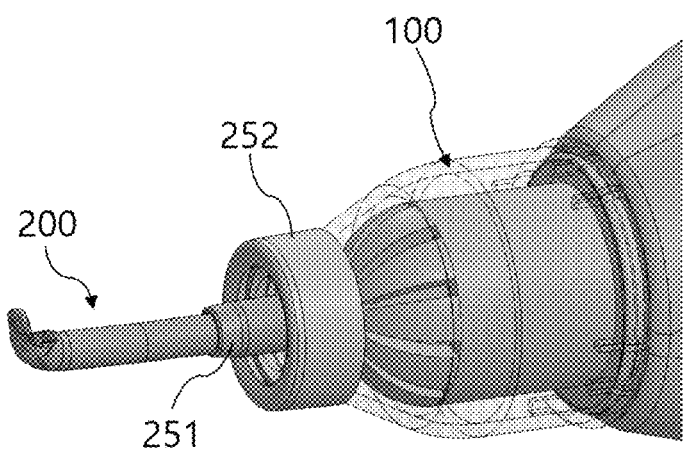
FIG. 10 is a drawing to illustrate important parts of an earwax removal device according to a third embodiment of the present invention.

FIG. 10 is a drawing to illustrate important parts of an earwax removal apparatus according to the third embodiment of the present invention.

The earwax removal apparatus according to the third embodiment of the present invention is intended for use in public places such as hair salons.

The earwax removal apparatus according to the third embodiment of the invention differs from the earwax removal apparatus according to the second embodiment of the invention described above in that the scrubbing head 210 and the wax pocket 120 are disposable, but the other components are substantially the same.

Since the earwax removal apparatus according to the third embodiment of the present invention is placed in a public place such as a hair salon, it is desirable that the scrubbing head 210 and the wax pocket 120 be disposable.

According to FIG. 10, the disposable scrubbing head 210 is detachably installed on the head attachment rod 251, and a soft contact portion 252 made of silicone or the like may be formed on one side of the wax pocket 120 (i.e., the portion in contact with the entrance of the ear canal).

The disposable wax pocket 120 and the scrubbing head 210 may each be made by compression molding paper. During the compression molding of the paper, the density and hardness of the paper, the surface roughness, and the absorbency of the paper may be adjusted so that the product may be produced in various shapes to suit the taste of the user.

This enables hygienic use of products in public places by individuals, enabling personal prevention against COVID-19, etc. and eco-friendly production of disposable products.

Figure 11:
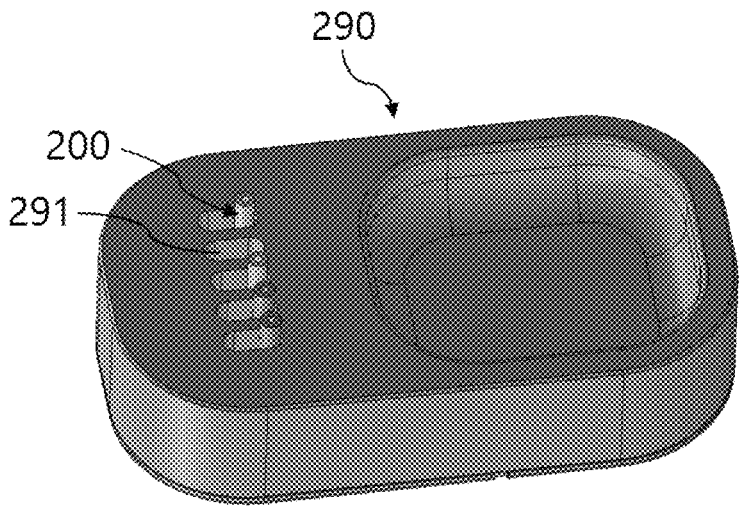
FIG. 11 is a diagram illustrating an example of a cleaning device capable of cleaning a head with a scrubbing head in embodiments of the present invention.

FIG. 11 is a diagram illustrating one example of a cleaning apparatus capable of cleaning a head having a scrubbing head 210 in embodiments of the present invention.

The cleaning apparatus 290 in FIG. 11 enables cleaning, such as disinfection using ultrasound, by plugging the head portion 200 inside the charging cradle. Of course, if the scrubbing head 210 is detachable from the head portion 200, only the scrubbing head 210 may be plugged in.

Inside the charging cradle, there is a separate cleaning container (space) for a cleaning solution, and the charging cradle is formed with an opening 291 through which the end of the head portion 200 (e.g., a scrubbing head with a tip 250), which may be stuck with earwax residue or the like, may be mounted to be immersed in the cleaning solution.

An ultrasonic vibrator or the like is placed inside the charging cradle and connected to the cleaning container, and ultrasonic vibrations are applied to the cleaning liquid so that the head portion 200 is cleaned.

On the other hand, in various embodiments of the earwax removal apparatus as described above, a function may be added that when the tip 250 enters the ear canal, the distance between the ear eardrum and the tip 250 is measured by infrared and ultrasonic waves or the like to prevent further entry if it is too close.

Furthermore, it is possible to remove the wax pocket 120 and insert an infrared body temperature measurement module so that body temperature measurement may be performed as an additional function.

Figure 12:
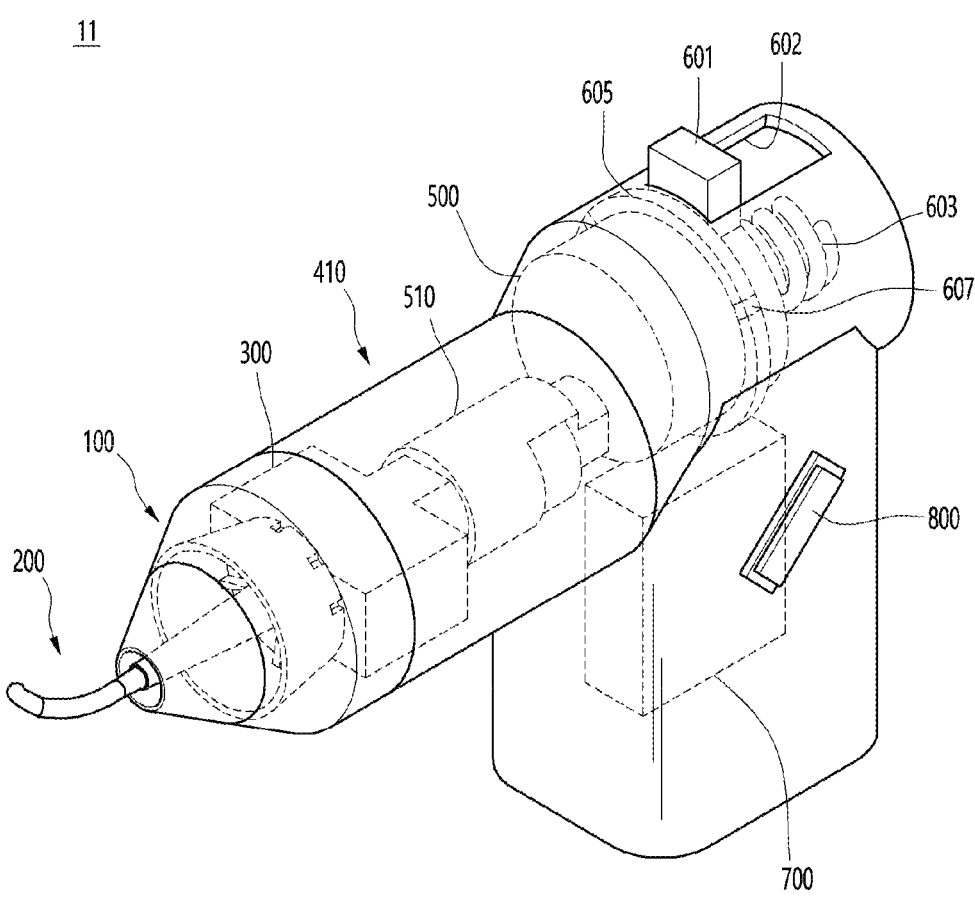
FIG. 12 is an internal perspective view of an earwax removal device according to the fourth embodiment of the present invention.
Figure 13:
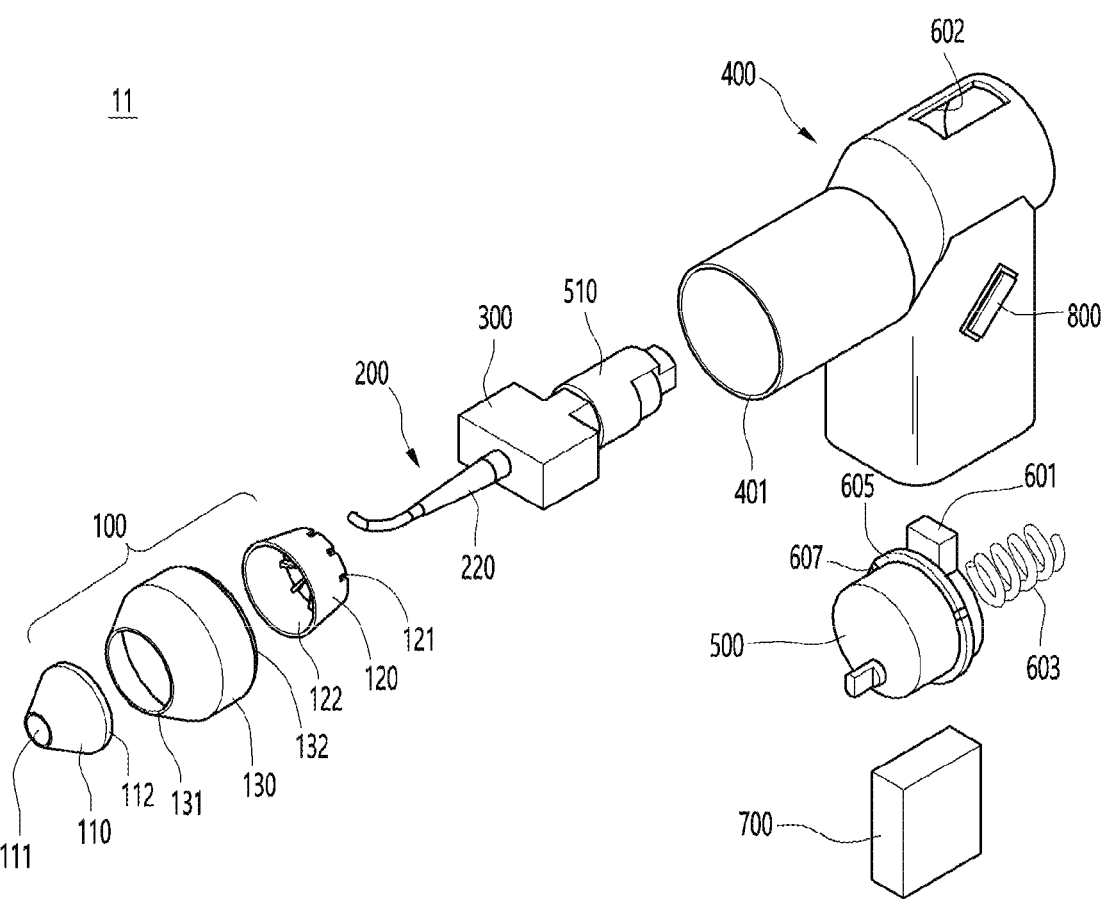
FIG. 13 is an exploded perspective view of an earwax removal device according to the fourth embodiment of the present invention.

FIG. 12 is an internal perspective view of the earwax removal apparatus 11 according to the fourth embodiment of the present invention, and FIG. 13 is a disassembled perspective view of the earwax removal apparatus according to the fourth embodiment of the present invention. For convenience of description, parts identical to the above-described embodiments are designated by the same drawing symbols, and parts common to the above-described embodiments are omitted from description.

More specifically, referring to FIGS. 12 and 13, the drive portion 600 of the earwax removal apparatus 11 according to the fourth embodiment of the present invention may be manually operated differently from the previous embodiments.

The actuation portion is connected to the head portion 200 and may include an externally exposed manual knob 601 for moving the head portion 200 forward and backward.

More specifically, the actuation portion may include the manual knob 601, a return spring 603, and a slide ring 605.

In one example, the manual knob 601 may be formed to protrude on one side of the motor 500.

In addition, an knob hole 602 may be formed on one side of the main body 400 such that the manual knob 601 is exposed to the outside.

That is, the motor 500 may be disposed inside the main body 400, and the manual knob 601 formed to protrude from the motor 500 may pass through the knob hole 602 and be exposed to the outside of the main body 400.

The knob hole 602 may be formed to have a predetermined length, which may guide forward and backward movement of the manual knob 601. That is, the manual knob 601 may be arranged to move forward and backward along the length of the knob hole 602.

When the user moves the manual knob 601 using a finger along the longitudinal direction of the knob hole 602, the head portion 200 associated with the manual knob 601 may be moved forward or backward inside the ear canal. That is, as described above, the head portion 200 of the present invention is connected to the pump 300, the pump 300 is connected to the motor 500 by the connector 510, and the motor 500 is connected to the manual knob 601, so that when the user moves the manual knob 601, the motor 500, the pump 300, and the head portion 200 may be moved forward or backward.

The motor 500, pump 300, and head portion 200 are integrated by the connector 510 so that they may be simultaneously moved forward or backward by manual operation of the manual knob 601.

In particular, the manual knob 601 may include a slide ring 605 provided to more easily move the manual knob 601. The slide ring 605 may include a plurality of rollers 607 that contact an inner circumferential surface of the main body 400 and are arranged to move along the inner circumferential surface. The rollers 607 may be spaced apart at predetermined intervals along the perimeter of the slide ring 605.

Further, the slide ring 605 is disposed around the outer periphery of the motor 500, and when the manual knob 601 is moved, the plurality of rollers 607 of the slide ring 605 rotate and move along the inner circumferential surface of the main body 400 to allow the user to more easily move the manual knob 601.

Additionally, the return spring 603 may be arranged such that when a user operates the manual knob 601 to advance the head portion 200, the return spring 603 may automatically return the head portion 200 to its original position when the user releases the finger.

In one example, the return spring 603 connects an inner side of the main body 400 and the first side of the motor 500, such that when no force is applied to the manual knob 601, the motor connected to the return spring 603 is moved by the return spring 603 to the inner side of the main body 400 (the backward direction side).

Therefore, a general user who is not sensitive to skin irritation may control the forward and backward speeds at a speed desired by the user, allowing instantaneous movement of the head portion 200 to occur, and has the effect of arbitrarily controlling the depth at which the head portion 200 is inserted into the ear canal and the number of insertions, etc.

On the other hand, the earwax removal apparatus 11 may be arranged so that the above-described drive portion 600 may be used by selecting a manual mode or an automatic mode according to a user by appropriately arranging the linear guide, the manual knob 601, the return spring 603, and the slide ring 605.

Here, the main body 400 may further include a mode selection portion (midway) arranged to allow a user to select a manual or automatic mode.

If the user selects the automatic mode, the linear guide described above is driven to slide the head portion 200 into the user's ear canal at a preset speed, and the head portion 200 enters the ear canal at the preset speed and removes earwax adhering to the walls of the ear canal using scrubbing and air blowing pressure.

If the user selects the manual mode, the user may manually operate the aforementioned manual knob 601 to slidingly move the head portion 200 into the ear canal to remove the earwax attached to the ear canal wall.

Meanwhile, a battery 700 may be disposed inside the main body 400 to electrically connect with the pump 300, the motor 500, and the drive portion 600 to provide power.

In addition, a switch (not shown) for operating the earwax removal apparatus 11 may be provided on the outer peripheral surface of the main body 400, and the earwax removal apparatus 11 may be operated according to an on/off operation of the switch.

Further, a mode selector (not shown) for selecting an automatic mode or a manual mode of the earwax removal apparatus 11 may be provided on the outer peripheral surface of the main body 400. In particular, depending on the mode selection, the drive portion 600 may be driven in the case of the automatic mode, and the user may operate the manual knob 601 in the case of the manual mode.

The earwax removal apparatus 11 of the present invention described above may be provided with the manual knob 601 on the upper part of the motor 500, a linear guide connected to the lower part of the motor 500, a pump 300 connected to the front (wax pocket side) of the motor 500, and a return spring 603 connected to the rear of the motor 500.

Thus, when the drive portion 600 is operated, the motor 500 connected to the drive portion 600 advances, the pump 300 connected to the motor 500 advances inside the apparatus, and the head portion 200 connected to the pump 300 advances outwardly through the collection hole 111 and may be inserted into the ear canal.

At this time, when the user operates via the manual knob 601, the motor 500 associated with the manual knob 601 is advanced, the pump 300 associated with the motor 500 is advanced inside the apparatus, the head portion 200 associated with the pump 300 is advanced outwardly through the collection hole 111 and may be inserted into the ear canal, and when the force applied to the manual knob 601 is released, the head portion 200 is retracted inside the apparatus by the return spring 603 to return to its original position.

Figure 14:
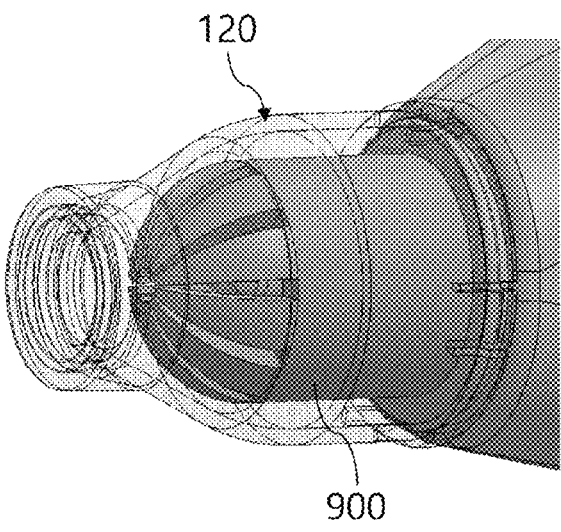
FIGS. 14 through 20 are drawings to illustrate a remover applicable to embodiments of the present invention.
Figure 15:
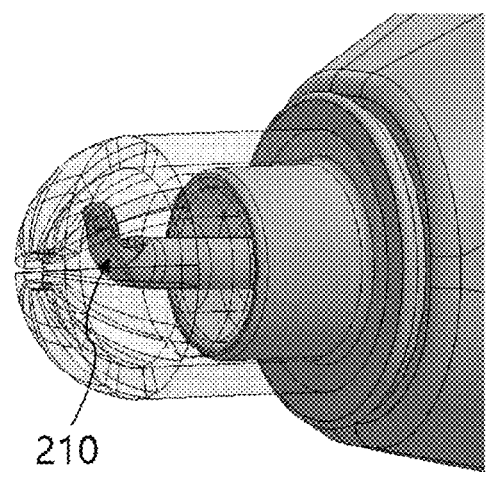
Figure 16:
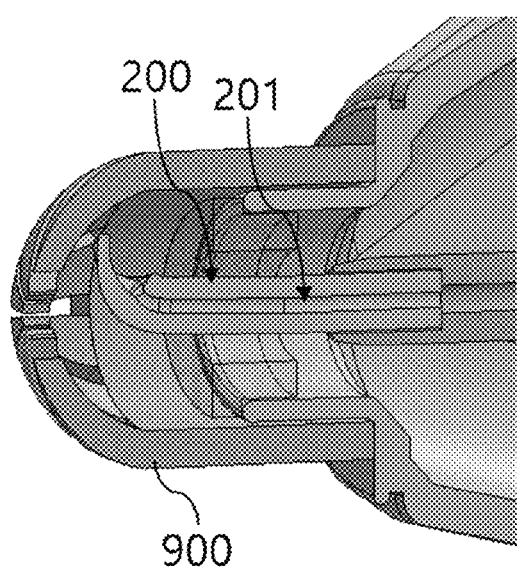
Figure 17:
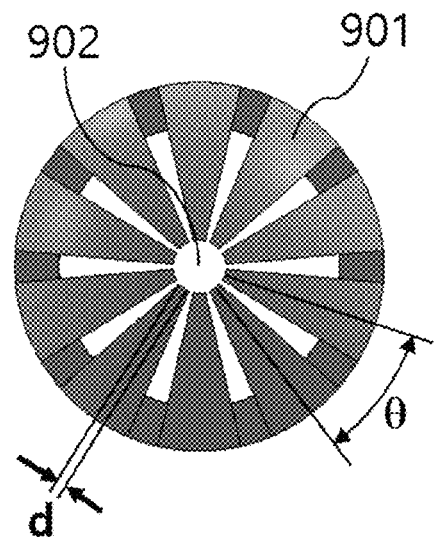
Figure 18:
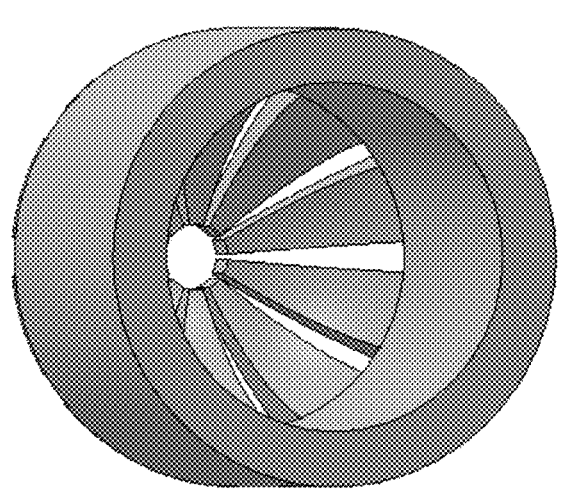
Figure 19:
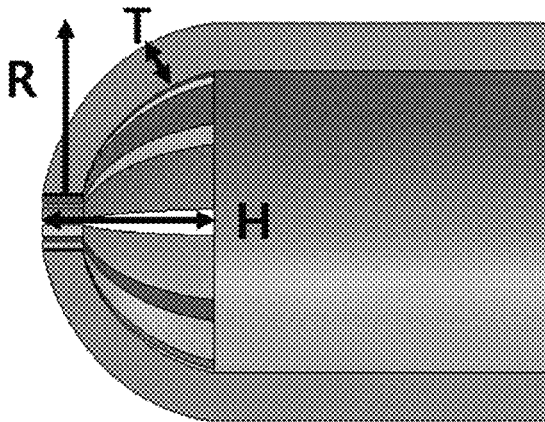
Figure 20:
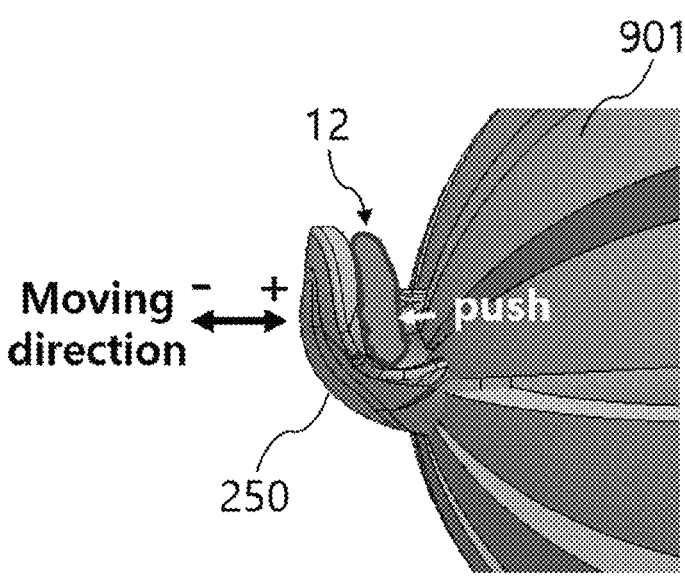

FIGS. 14 through 20 are drawings to illustrate a remover 900 applicable to embodiments of the present invention, wherein FIG. 14 is a drawing showing only the area where the remover 900 is installed in an earwax removal apparatus, and FIG. 15 is a drawing showing the wax pocket 120 shown in FIG. 14 removed and the scrubbing head 210 positioned inside the remover, FIG. 16 is a cross-sectional view of FIG. 15, FIG. 17 is a front view of the remover 900, FIG. 18 is a perspective view of the remover 900 from the rear, FIG. 19 is a cross-sectional view of the remover 900, and FIG. 20 is a diagram to illustrate the operation of the remover 900. For ease of description, parts identical to the above-described embodiments use the same drawing symbols, and parts common to the above-described embodiments are omitted from description.

Referring to FIGS. 14 through 20, the remover 900 effectively removes wet earwax, which has a high viscosity and adhesion, from the tip 250 of the scrubbing head 210 so that it may be dropped inside the wax pocket 120.

The remover 900 may be removably installed inside the wax pocket 120.

Since wet earwax removed by tip 250 of scrubbing head 210 sticks to scrubbing head 210 and does not fall off on its own, use of the remover 900 effectively allows wet earwax 12 stuck to tip 250 of scrubbing head 210 to fall off and be captured inside wax pocket 120.

The remover 900 has a plurality of curved elastic ribs 901 having a width D similar to the width inside the tip 250 of the scrubbing head 210.

Each elastic rib 901 is formed equidistantly spaced from each other on one side (e.g., the front) of the hollow main body of the remover 900, but is formed with a constant curvature, i.e., one end of each elastic rib 901 is formed integrally with the main body of the remover 900, and the other end of each elastic rib 901 is curved (bent) away from the body of the remover 900 with a constant curvature.

At this time, the width of one end of each elastic rib 901 integrally formed with the body of the remover 900 is larger than the width of the other end.

Furthermore, the other end of each elastic rib 901 is spaced apart from the other end of the elastic rib 901 in an opposite position by a certain distance. As a result, a passage hole 902 is formed in the remover 900 through which the scrubbing head 210 may exit the outside of the remover 900 or enter inside of the remover 900 when the scrubbing head 210 performs a linear motion.

The material of the remover 900 may be any soft material having a Shore A hardness between 60 and 90.

Furthermore, as shown in FIG. 19, the stiffness of each elastic rib 901 may be determined by adjusting the hardness of the remover 900 and the thickness T of the elastic rib 901, the length R in the vertical direction from the other end of the elastic rib 901 to the body, and the length H in the horizontal direction from the other end of the elastic rib 901 to the first end.

In particular, it is desirable to design the above-described stiffness to be equal to or less than the stiffness of the tip 250 of the scrubbing head 210. In this way, when the scrubbing head 210 performs a linear motion in the "+ moving direction" as shown in FIG. 20, the elastic ribs 901 in contact with the tip 250 of the scrubbing head 210 may bend and accumulate elastic force, and the accumulated elastic force may effectively push off the wet earwax 12 adhering to the tip 250.

Subsequently, when the scrubbing head 210, which has entered the interior of the remover 900, makes a linear motion in the "-moving direction" to enter the ear canal again and exits through the passage hole 902 of the remover 900, at this time the wet earwax 12 on the scrubbing head 210 was already removed, so wet earwax inside the ear canal may be easily scraped off again.

When the scrubbing head 210 is rotated by a certain angle θ, the tip 250 of the scrubbing head 210 may contact any one of elastic ribs 901, and when the scrubbing head 210 is subjected to linear motion in both directions (+, – moving directions), the tip 250 of the scrubbing head 210 may effectively remove all of the wet earwax around the entire circumference of the ear canal (360 degrees).

Furthermore, if this type of remover structure is placed in two or more layers, the effect may be improved by more than two times, as the wet earwax is removed more than once for a single linear motion.

Figure 21:
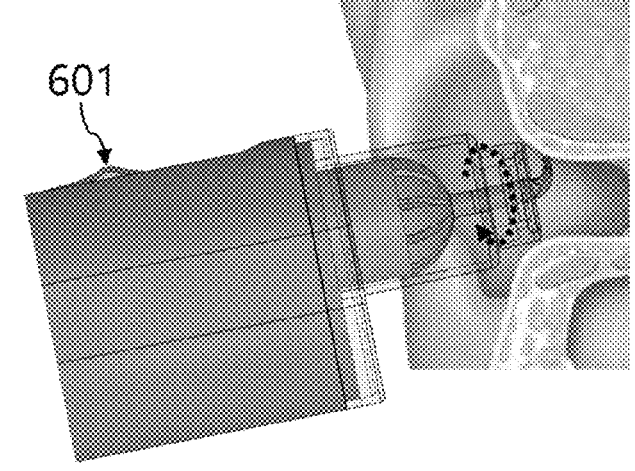
FIGS. 21 to 23 are drawings to illustrate the operation of an earwax removal device according to the fourth embodiment of the present invention.
Figure 22:
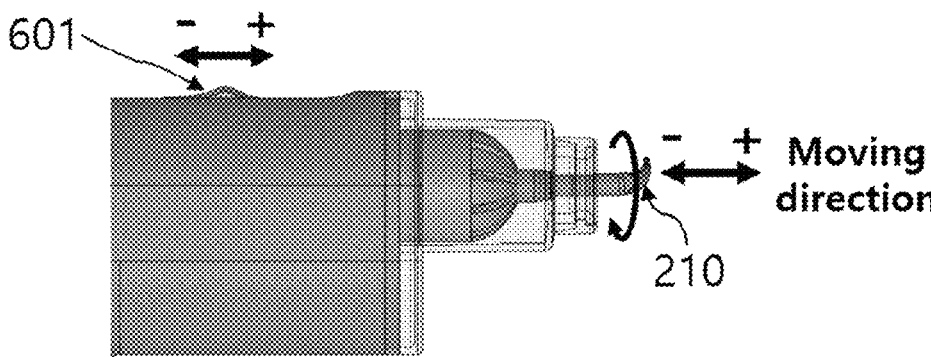
Figure 23:
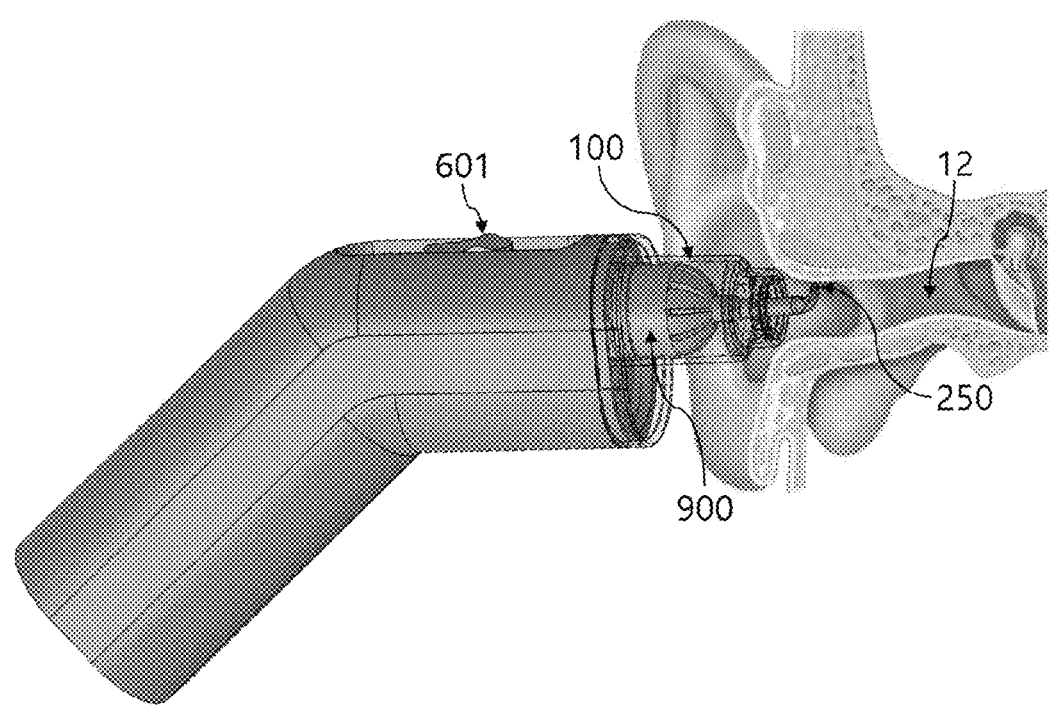

FIGS. 21 to 23 are drawings to illustrate the operation of an earwax removal apparatus according to the fourth embodiment of the present invention.

In an earwax removal apparatus in which a user removes earwax (e.g., wet earwax) by moving the manual knob 601 to cause a linear motion (+, – moving direction) of the head portion (in particular, the scrubbing head 210), it is desirable to periodically rotate the scrubbing head 210 at a certain angle to remove all the earwax on the wall of the cylindrical ear canal, When a user directly holds the earwax removal apparatus by hand and rotates the earwax removal apparatus, it is not only difficult to operate the manual knob 601, but also difficult to periodically rotate the scrubbing head 210 at a certain angle.

In particular, in the case of an earwax removal apparatus in which the user moves the manual knob 601 to cause a linear motion (+, – moving direction) of the scrubbing head 210 to remove earwax, when the tip 250 of the scrubbing head 210 enters the ear canal, due to the anatomical characteristics of the ear, it hits the protrusion on the entrance of the ear canal and gets stuck (see FIG. 21). This results in a rejection reaction by the user.

Accordingly, the present invention rotates the scrubbing head 210 by a predetermined angle (e.g., 10 degrees to 30 degrees) each time the tip 250 approaches the entrance of the ear canal to enter the ear canal (see FIG. 22), thereby allowing the tip 250 to enter the ear canal without getting caught on the entrance protrusion of the ear canal (see FIG. 23). For example, the distance between the entrance of the ear canal and the tip 250 may be detected using infrared and ultrasonic sensors, and when the distance is within a certain range, the scrubbing head 210 may be rotated by a predetermined angle (e.g., 10 degrees to 30 degrees) to allow the tip 250 to enter the interior of the ear canal without catching on the entrance protrusion of the ear canal.

Then, in the present invention, the scrubbing head 210 may be automatically rotated by a predetermined angle via sensing the movement of the manual knob 601 through an internal sensor (not shown) (e.g., a position sensor, an infrared sensor, or the like) that may sense the movement of the manual knob 601 without having to manually rotate the earwax removal apparatus.

In other words, in one example of a method of removing earwax in the fourth embodiment of the present invention, whenever the tip 250 of the scrubbing head 210 approaches the entrance of the ear canal to enter the ear canal, the scrubbing head 210 rotates a predetermined angle (e.g., about 10 degrees to 30 degrees) to enter the ear canal, After entering, the scrubbing head 210 may simply scrape the earwax to the outside of the ear canal without any further rotation of the scrubbing head 210 as the user manipulates the manual knob 601 to move the scrubbing head 210 forward/backward. In this method, when a user moves the manual knob 601 (moves in a +, − direction) using a finger, the scrubbing head 210 of the head portion 200 associated with the manual knob 601 moves forward or backward inside the ear canal. Here, when the user releases the finger, the head portion 200 is automatically returned to the original position by the return spring 603.

In another example of a method for removing earwax in the fourth embodiment of the present invention, whenever the tip 250 of the scrubbing head 210 approaches the entrance of the ear canal to enter the ear canal, the scrubbing head 210 rotates a predetermined angle (e.g., about 10 degrees to 30 degrees) to enter the ear canal, and after entering, the head portion (esp, scrubbing head 210) performs an earwax removal operation on the wall surface of the ear canal, which is divided into a plurality of tracks, by entering a predetermined unit depth through any one of the plurality of tracks, moving to an adjacent track by rotating a certain angle (δ), and then retreating to the outside of the ear canal through the adjacent track, and the head performs the earwax removal operation repeatedly on all tracks at the current depth entered and on all tracks at subsequent depths according to the subsequent entry by a unit depth, thereby scraping the wet earwax to the outside of the ear canal.

This is a very important ergonomic feature that allows the user to use the product without resistance and discomfort.

Figure 24:
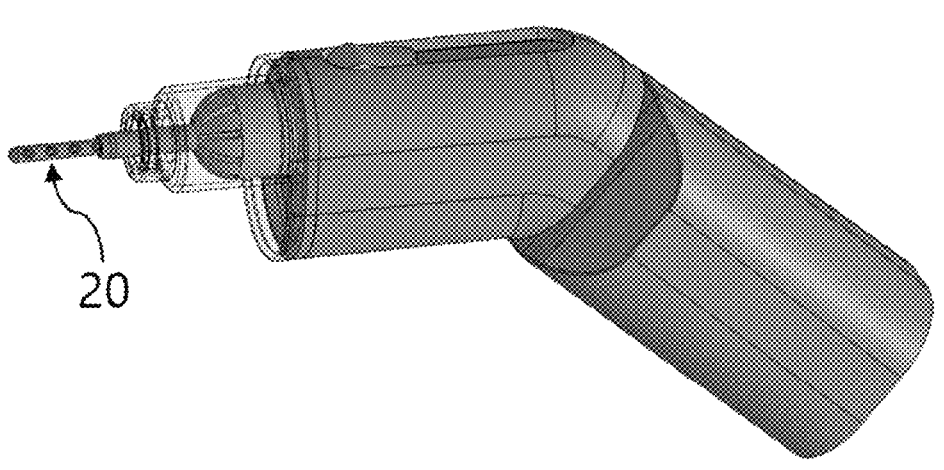
FIGS. 24 through 27 are drawings to illustrate other examples of dry-only heads applicable to embodiments of the present invention.
Figure 25:
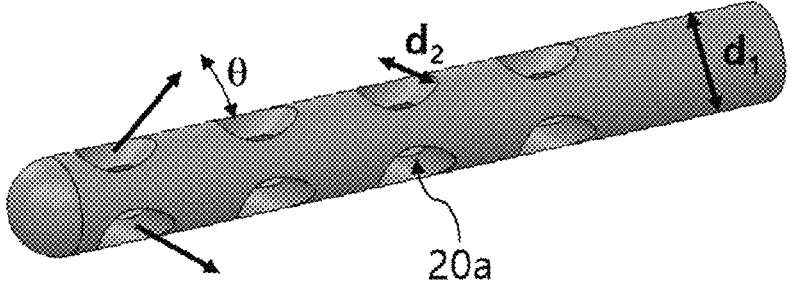
Figure 26:
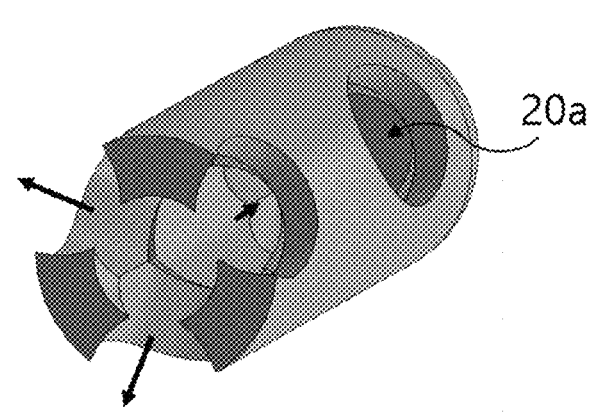
Figure 27:
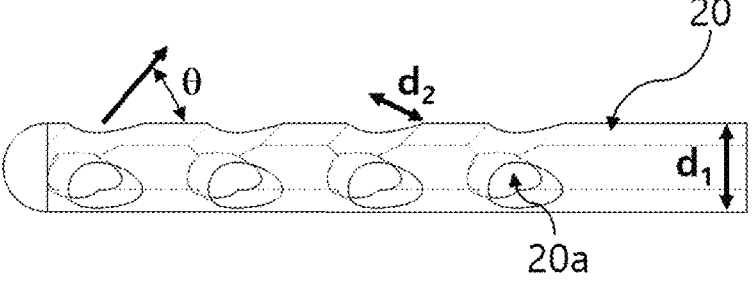

FIGS. 24 through 27 are drawings to illustrate one example of dry-only head 20 applicable to embodiments of the present invention, wherein FIG. 24 is a drawing illustrating one example of an earwax removal apparatus employing a dry-only head 20, FIG. 25 is a magnified view of the dry-only head 20 of FIG. 24, FIG. 26 is a cross-sectional view of the dry-only head 20 of FIG. 25, and FIG. 27 is a variant of the dry-only head 20 of FIG. 24. The variant of FIG. 27 differs slightly in the shape of the hole 20a when compared to FIG. 25, but is otherwise identical.

The conventional method of preventing otolaryngological otitis externa involves drying the ear with a hair dryer at a distance of about 30 cm from the ear, which is very inconvenient to carry and use.

In addition, the amount of air flow directly entering the ear canal is greatly limited by the "area×wind speed" of the ear canal, which is dependent on the area of the ear canal. As a result, it is difficult to effectively and quickly dry the inside of the ear canal.

Since 5-10% of the world's population suffers from frequent otitis externa, there is a need for an easy, fast, and effective way to dry the ear canal after swimming, showering, or washing the face.

Accordingly, the present invention provides a dry-only head 20 (also known as a "dry tip") for drying the ear canal for use with an earwax removal apparatus (see FIGS. 24 through 27).

The dry-only head 20 of FIGS. 24 through 27 is made of a biocompatible soft material (e.g., rubber and silicone) with a thin diameter d1 (approximately 2 to 3 millimeters (mm)) to allow for comfortable and easy entry into the ear canal.

The dry-only head 20 of FIGS. 24 through 27 may have the scrubbing head 210 of the head portion 200 removed and mounted in its place.

In particular, the dry-only head 20 of FIGS. 24 through 27 is formed in the form of a thin tube that may easily enter the ear canal, and by having a plurality of holes 20a having a diameter d2 (approximately 0.1 to 1.5 mm or so) and an angle θ between 45° and 90° on the wall of the tube, it is possible to overcome the disadvantage of a hair dryer that does not effectively introduce wind into the ear canal by blowing wind directly onto the wall of the ear canal via the thin tube. In addition, the pressure of the wind is directed toward the ear canal wall and the ear canal entrance, so that the water droplets inside the ear canal may be quickly removed to the outside of the ear, and at the same time, the moisture may also effectively escape to the outside.

Therefore, even if it is difficult to drain the water in the user's ear after swimming, the user may quickly remove the water in the ear and at the same time, the pressure is not transmitted directly to the eardrum, so the user may dry the inside of the ear canal very comfortably and safely.

Existing similar products have the disadvantage of blowing air directly into the ear from the entrance of the ear canal, so that the entire ear canal may easily become an obstructed space, and the resulting increased pressure may be directly applied to the ear drum.

The dry-only head 20 of FIGS. 24 to 27 greatly compensates for these disadvantages and greatly improves drying efficiency.

Figure 28:
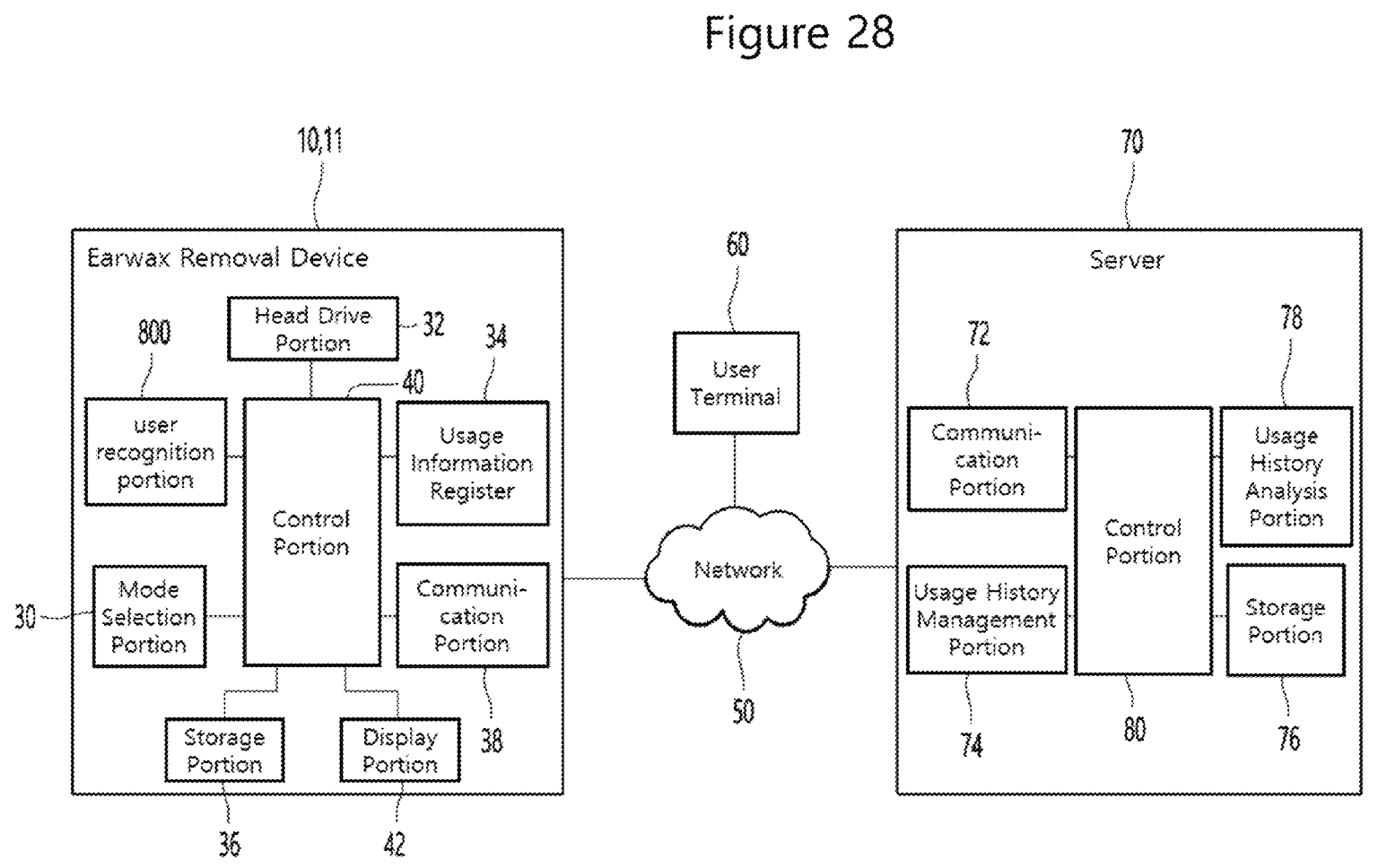

FIG. 28 is a system configuration diagram to illustrate the interaction between an earwax removal apparatus according to the present invention and a server and a user terminal.

The system of FIG. 28 may include an earwax removal apparatus 10, 11, a network 50, a user terminal 60, and a server 70.

The earwax removal apparatuses 10, 11 may include a mode selection portion 30, a head drive portion 32, a usage information register 34, a storage portion 36, a communication portion 38, a control portion 40, a display portion 42, and a user recognition portion 800. While only one earwax removal apparatus 10, 11 is shown in FIG. 28, it should be understood that there may be multiple apparatus.

The user recognition portion 800 is arranged to store and recognize apparatus usage information of a user, as previously described, and may be a fingerprint recognition apparatus (fingerprint sensor), and may be disposed on an outer surface of the main body 400. For example, the user recognition portion 800 may be disposed at a location where the user's thumb reaches when the user grips the earwax removal apparatus 10, 11.

The mode selection portion 30 may select an automatic mode or a manual mode.

Accordingly, a button (not shown) may be installed on the main body 400 of the earwax removal apparatus 10, 11 to enable selection of the automatic mode or the manual mode.

The above-described remover 900 may be used in both automatic and manual modes.

Additionally, if desired, a dry mode may be added to the mode selector 30 to enable the use of the dry-only head 20 of FIGS. 24 through 27. Here, in dry mode, the dry-only head 20 is preferably used to dry the inside of the ear canal.

The head drive portion 32 may drive the head portion 200 in conjunction with the pump 300 and motor 500.

The head drive portion 32 may drive the head portion 200 according to a mode selected in the mode selection portion 30.

For example, when the automatic mode is selected, the head drive portion 32 may drive the linear guide described above to automatically slide the head 200 into the user's ear canal at a preset speed to remove earwax adhering to the walls of the ear canal using scrubbing and air blowing pressure. In other words, when the automatic mode is selected, the head drive portion 32 may operate to rotate the head portion 200 by a predetermined angle (e.g., 10 to 30 degrees) as the scrubbing head 210 of the head portion 200 reaches the entrance of the ear canal to prevent the scrubbing head 210 from getting stuck on the protrusion of the entrance of the ear canal, and also to automatically perform the subsequent earwax removal operation. Here, the automatic wet earwax removal operation (as described in FIG. 7) may mean that the head portion (in particular, the scrubbing head 210) repeatedly performs the operation of entering a predetermined unit depth through any one of the multiple tracks against a wall surface of the ear canal comprising a plurality of tracks, moving to an adjacent track by rotating a certain angle (δ), and then retracting to the outside of the ear canal through the adjacent track.

On the other hand, when the manual mode is selected, when the user manually operates the manual knob 601, the head drive portion 32 may slidingly move the head portion 200 into the ear canal to remove the earwax attached to the wall of the ear canal. In other words, when the manual mode is selected, the head drive portion 32 operates such that the back and forth movement and rotation of the head portion 200 is in accordance with the user's operation. When the manual knob 601 is operated by the user, the motor 500 associated with the manual knob 601 is advanced, and the pump 300 associated with the motor 500 is advanced inside the apparatus 10, 11), the head portion 200 connected to the pump 300 advances outwardly through the collection hole 111 and is inserted into the ear canal, and when the force applied to the manual knob 601 is released, the head portion 200 is retracted inside the apparatus by the return spring 603 so that the head portion 200 is returned to its original position.

Of course, even in the manual mode described above, the head drive portion 32 may automatically rotate the head portion 200 by a predetermined angle (such as 10 degrees to 30 degrees) when the scrubbing head 210 of the head portion 200 reaches the entrance of the ear canal. This is to allow the tip 250 of the scrubbing head 210 of the head portion 200 to enter the ear canal without catching on a protrusion on the entrance of the ear canal.

The usage information register 34 stores apparatus usage information of the user recognized by the user recognition portion 800, such as the number of times the user uses the apparatus, the time of use, and the like, in the storage part 36.

The storage portion 36 may store the user's apparatus usage information from the usage information register 34.

The communication portion 38 may transmit the user's apparatus usage information stored in the storage part 36 to the server 70 via the network 50. For this purpose, the communication portion 38 includes a wireless communication module such as Wi-Fi or the like.

The control portion 40 controls the overall operation of the above-described earwax removal apparatuses 10, 11.

The display portion 42 may display usage history analysis results (e.g., calibration information) or warnings from the server 70.

The network 50 may be implemented as any type of wireless network, such as a mobile radio communication network, satellite communication network, Bluetooth, Wireless Broadband Internet (Wibro), High Speed Downlink Packet Access (HSDPA), Wi-Fi, Long Term Evolution (LTE), or the like.

Additionally, the network 50 may be implemented as a wired network, such as a local area network (LAN), a wide area network (WAN), or a value added network (VAN).

Optionally, the network 50 may be a mixed wired and wireless network.

The user terminal 60 may communicate with the server 70 over the network 50.

The user terminal 60 may receive usage history analysis results (e.g., calibration information) for the corresponding user from the server 70 over the network 50 and view them through an application on the terminal.

For example, the user terminal 60 may be implemented as a portable terminal or a portable computer. A handheld terminal is a wireless communication apparatus that is portable and mobile, and may include any kind of handheld-based wireless communication apparatus, such as a Personal Communication System (PCS), Global System for Mobile communications (GSM), Personal Digital Cellular (PDC), Personal Handyphone System (PHS), Personal Digital Assistant (PDA), International Mobile Telecommunication (IMT)-2000, Code Division Multiple Access (CDMA)-2000, W-Code Division Multiple Access (W-CDMA), Wireless Broadband Internet (Wibro) terminal, and the like. A portable computer may include a notebook, laptop, or the like.

The user terminal 60 may also be any kind of smart apparatus, such as a smartphone, smart notebook, tablet PC, wearable computer, etc.

The server 70 may include a communication portion 72, a usage history management portion 74, a storage portion 76, a usage history analysis portion 78, and a control portion 80.

The communication portion 72 may communicate with the earwax removal apparatuses 10, 11 via the network 50.

In addition, the communication portion 72 may communicate with the user terminal 60 over the network 50.

The usage history management portion 74 may manage the user's apparatus usage information from the one or more earwax removal apparatuses 10, 11 received via the communication portion 72 as a user-specific usage history. That is, the usage history management portion 74 may store the user-specific usage history in the storage portion 76.

The storage portion 76 stores the user-specific usage history by the usage history management portion 74.

In other words, the storage portion 76 stores user-specific usage history, such as the number of times the apparatus is used, the time of use, and the like, separately for each user.

Based on the user-specific usage history stored in the storage portion 76, the usage history analysis portion 78 may analyze the optimal rotation speed (i.e., the rotation speed of the scrubbing head 210), wind strength (i.e., the blowing strength of the dry-only head), etc. for each user and output corresponding calibration information.

Here, the calibration information may be transmitted to the user's earwax removal apparatuses 10, 11 or the user terminal 60 via the network 50.

The calibration information described above may be referred to as a usage history analysis result.

Of course, the usage history analysis portion 78 may analyze the user's usage history and issue appropriate warnings. In this case, the warning is for the purpose of preventing cerumen impaction (excessive earwax) for a user who is prone to cerumen impaction, and a notification message may be sent to the user's earwax removal apparatuses 10, 11 or the user terminal 60 to encourage periodic use of the apparatus.

The control portion 80 may control the overall operation of the server 70 described above.

As described above, the best embodiments have been disclosed in the drawings and specifications. While certain terms are used herein, they are used solely for the purpose of describing the invention and are not intended to limit the meaning or scope of the invention as set forth in the claims. Accordingly, one of ordinary skill in the art will understand that various modifications and equivalents of other embodiments are possible. Accordingly, the true technical scope of the invention should be determined by the technical ideas of the appended claims.

What is claimed is:

1. An earwax removal apparatus comprising:
a wax pocket defining an interior;
a head portion including a scrubbing head having a tip, the head portion being configured to move from the interior of the wax pocket to outside of the wax pocket and move from the outside to inside of the wax pocket; and
a remover removably mounted inside the wax pocket, the remover comprising a hollow body defining a passage hole and a plurality of curved elastic ribs arranged on one side of the hollow body,
wherein, for each elastic rib, a first end of the elastic rib is integrally formed with the hollow body and a second end of the elastic rib is curved away from the hollow body with a constant curvature, and second ends of opposing elastic ribs are spaced apart to define the passage hole,
wherein, during a linear motion of the scrubbing head into the remover, the plurality of curved elastic ribs bend to accumulate elastic force and the accumulated elastic force dislodges earwax from the tip of the scrubbing head of the head portion such that the earwax falls into the interior of the wax pocket,
wherein the plurality of elastic ribs are mutually equidistantly spaced apart from each other on one side of the hollow body of the remover,
wherein the stiffness of each elastic rib of the remover is equal to or less than the stiffness of the tip of the scrubbing head.

2. The earwax removal apparatus of claim 1,
wherein a material of the remover is a soft material.

3. The earwax removal apparatus of claim 1, further comprising:
a dry-only head mountable on the earwax removal apparatus and capable of entering an ear canal and blowing air directly onto a wall of the ear canal.

4. The earwax removal apparatus of claim 3,
wherein the dry-only head is formed in the form of a conduit and a plurality of holes are formed in a wall of the conduit.

5. The earwax removal apparatus of claim 4,
wherein the dry-only head directs the pressure of air toward the wall of the ear canal and an entrance of the ear canal, thereby removing water droplets inside the ear canal to the outside of the ear and allowing moisture to escape to the outside.

6. The earwax removal apparatus of claim 1, further comprising:
an oily earwax removal portion configured to remove hardened oily earwax by injecting a wax-dissolving liquid into an ear canal through a spray hole of the scrubbing head of the head portion.

7. The earwax removal apparatus of claim 6,
wherein the oily earwax removal portion injects the wax-dissolving liquid into a space connected to an inner passage of the head portion through a fill hole openable on an outside of the earwax removal apparatus.

8. An earwax removal apparatus comprising:
the earwax removal apparatus of claim 1; and
a head driving portion configured to automatically drive a head portion.

9. The earwax removal apparatus of claim 8,
wherein the head driving portion is configured to rotate the head portion by a predetermined angle as the scrubbing head of the head portion approaches an ear canal entrance, thereby preventing the head portion from being caught on a protrusion of the ear canal entrance.

10. The earwax removal apparatus of claim 9,
wherein an automatically occurring earwax removal operation comprises the head portion entering a predetermined unit depth through any one of multiple tracks of a wall surface of the ear canal comprising a plurality of tracks, moving to an adjacent track by a predetermined angle of rotation, and then retracting through the adjacent track to outside of the ear canal,
wherein the head portion performs the earwax removal operation repeatedly on all tracks at a current depth entered and on all tracks at subsequent depths following subsequent entry by a unit depth.

11. The earwax removal apparatus of claim 8,
wherein the head driving portion slidingly moves the head portion into an ear canal to remove earwax adhering to a wall surface of the ear canal in response to a user's manipulation of a manipulation knob, and reverses the head portion to return to an original position as a force applied to the manipulation knob is released.

12. The earwax removal apparatus of claim 11,
wherein the head driving portion automatically rotates the head portion a predetermined angle when the scrubbing head is proximate to an ear canal entrance.

13. An earwax removal apparatus comprising:
the earwax removal apparatus of claim 1; and
a user recognition portion disposed within reach of a user's fingers when the user grasps the earwax removal apparatus and configured to allow usage information of the earwax removal apparatus to be stored in the earwax removal apparatus or a server outside.

14. The earwax removal apparatus of claim 13,
wherein the user recognition portion includes a jog switch.

15. The earwax removal apparatus of claim 14,
wherein the user recognition portion resets an automatic motion speed of the head portion to a user-selected speed via the jog switch, and stores the user-selected speed on the earwax removal apparatus or an external server such that the user-selected speed is applied when the earwax removal apparatus is reused.

\* \* \* \* \*